US007870009B2

(12) United States Patent
Patterson

(10) Patent No.: US 7,870,009 B2
(45) Date of Patent: *Jan. 11, 2011

(54) COMPUTERIZED SYSTEM AND METHODS FOR GENERATING AND PROCESSING INTEGRATED TRANSACTIONS FOR HEALTHCARE SERVICES

(75) Inventor: Neal L. Patterson, Belton, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1094 days.

This patent is subject to a terminal disclaimer.

(21) Appl. No.: 11/326,734

(22) Filed: Jan. 6, 2006

(65) Prior Publication Data

US 2006/0259324 A1 Nov. 16, 2006

Related U.S. Application Data

(60) Provisional application No. 60/651,503, filed on Jan. 6, 2005.

(51) Int. Cl.
*G06Q 50/00* (2006.01)
*G06F 19/00* (2006.01)
(52) U.S. Cl. .................................... 705/3; 705/2; 705/4
(58) Field of Classification Search .................. 705/2–4
See application file for complete search history.

(56) References Cited

U.S. PATENT DOCUMENTS 4,491,725 A   1/1985   Pritchard
5,253,164 A  10/1993   Holloway et al.

(Continued)

FOREIGN PATENT DOCUMENTS

WO   WO 9701141 A1 *   1/1997

OTHER PUBLICATIONS

"Tiered Quality Strategies: Definitions and State Systems"; National Child Care Information Center; Jun. 2004.*

(Continued)

*Primary Examiner*—Luke Gilligan
*Assistant Examiner*—Anita Molina
(74) *Attorney, Agent, or Firm*—Shook, Hardy & Bacon L.L.P.

(57) ABSTRACT

A method for adjudicating and reimbursing a care provider for services provided for a clinical event is provided. The method includes the step of receiving a transaction having a number of clinical data elements. The method also includes the steps of accessing a data store including payer information and determining whether the transaction is eligible for reimbursement by at least one payer. The method also includes the steps of accessing a first knowledge base comprising evidence-based standards for providing medically appropriate care and selectively performing analysis of the clinical data elements of the transaction against at least one standard to determine if the care provided is medically appropriate. The method further includes the steps of accessing a second knowledge base containing at least one criterion for assessing quality of care and selectively performing analysis of the clinical data elements of the transaction against the at least one criterion to determine if the care provided is medically appropriate. Also, the method includes determining a level of reimbursement based on the medical appropriateness and quality of the care provided and authorizing reimbursement of the care provider from at least one payer.

16 Claims, 12 Drawing Sheets

U.S. PATENT DOCUMENTS

| | | | |
|---|---|---|---|
| 5,301,105 A | | 4/1994 | Cummings |
| 5,519,607 A | * | 5/1996 | Tawil ............................. 705/2 |
| 5,544,044 A | * | 8/1996 | Leatherman ................... 705/3 |
| 5,706,441 A | | 1/1998 | Lockwood |
| 6,208,973 B1 | * | 3/2001 | Boyer et al. .................... 705/2 |
| 6,230,142 B1 | * | 5/2001 | Benigno et al. ................ 705/3 |
| 6,263,330 B1 | | 7/2001 | Bessette |
| 6,283,761 B1 | | 9/2001 | Joao |
| 2002/0062224 A1 | | 5/2002 | Thorsen et al. |
| 2002/0077869 A1 | | 6/2002 | Doyle et al. |
| 2002/0111826 A1 | * | 8/2002 | Potter et al. .................... 705/2 |
| 2002/0147617 A1 | | 10/2002 | Schoenbaum et al. |
| 2003/0009355 A1 | | 1/2003 | Gupta |
| 2003/0149594 A1 | | 8/2003 | Beazley et al. |
| 2003/0171953 A1 | | 9/2003 | Narayanan et al. |
| 2003/0191665 A1 | | 10/2003 | Fitzgerald et al. |
| 2003/0191667 A1 | | 10/2003 | Fitzgerald et al. |
| 2003/0191669 A1 | | 10/2003 | Fitzgerald et al. |
| 2003/0195771 A1 | | 10/2003 | Fitzgerald et al. |
| 2003/0216939 A1 | | 11/2003 | Bito et al. |
| 2004/0064386 A1 | | 4/2004 | Goguen et al. |
| 2004/0073456 A1 | | 4/2004 | Gottlieb et al. |
| 2004/0117215 A1 | | 6/2004 | Marchosky |
| 2004/0128165 A1 | | 7/2004 | Block et al. |
| 2004/0172313 A1 | | 9/2004 | Stein et al. |
| 2004/0193451 A1 | | 9/2004 | McNair |
| 2004/0236602 A1 | | 11/2004 | Greene |
| 2004/0249673 A1 | * | 12/2004 | Smith .............................. 705/2 |
| 2005/0149359 A1 | * | 7/2005 | Steinberg et al. ............... 705/2 |
| 2005/0216312 A1 | * | 9/2005 | Bellin et al. .................... 705/3 |
| 2005/0251416 A1 | | 11/2005 | Greene |
| 2006/0282286 A1 | * | 12/2006 | Faris et al. ...................... 705/2 |

OTHER PUBLICATIONS

Notice of Allowance, mailed Jul. 22, 2010, in U.S. Appl. No. 11/327,223, 21 pp.

Managed Care in Transition, Apr. 5, 2001, The New England Journal of Medicine, vol. 344, No. 14, 8 pp.

Form HCFA-1500, Approved Aug. 1988, Revision Date Dec. 1990, 2 pp.

Final Office Action, mailed May 26, 2009, re U.S. Appl. No. 11/327,223, 16 pp.

Final Office Action, mailed Aug. 21, 2009, re U.S. Appl. No. 11/327,055, 25 pp.

Final Office Action, mailed Feb. 1, 2010, re U.S. Appl. No. 11/326,746, 9 pp.

Final Office Action, mailed Mar. 2, 2010, re U.S. Appl. No. 11/327,223, 14 pp.

Office Action, mailed Mar. 5, 2008, re U.S. Appl. No. 11/327,055, 4 pp.

Office Action, mailed Dec. 10, 2008, re U.S. Appl. No. 11/327,055, 34 pp.

Office Action, mailed Jan. 2, 2009, re U.S. Appl. No. 11/327,223, 17 pp.

Office Action, mailed Jun. 25, 2009, re U.S. Appl. No. 11/326,746, 11 pp.

Office Action, mailed Oct. 14, 2009, re U.S. Appl. No. 11/327,223, 13 pp.

Office Action, mailed Feb. 19, 2010, re U.S. Appl. No. 11/327,055, 16 pp.

Notice of Allowance, mailed Sep. 16, 2010, in U.S. Appl. No. 11/327,055, 18 pp.

* cited by examiner

| CLINICAL EVENT DETAILS | | | | | |
|---|---|---|---|---|---|
| PERSON IDENTIFICATION | | | | | |
| | | NAME: | JOHNSON, RICHARD, L. | | |
| | | MOTHER'S MAIDEN NAME: | JONES | | |
| | | BIRTH DATE AND TIME . . . | | | |
| VISIT IDENTIFICATION | | | | | |
| | | IDENTIFIER: | 12345 | | |
| | | ADMIT REASON: | KNEE ARTHROSCOPY | | |
| | | CLASS CODE . . . | | | |
| ALLERGIES | | | | | |
| | | ALLERGEN CODING METHOD: | | | |
| | | ALLERGEN TYPE CODE: | A012 - ASPIRIN | | |
| | | ALLERGEN CODE/MNEMONIC/DESCRIPTION . . . | | | |
| PATIENT ADVERSE REACTIONS | | | | | |
| | | ALLERGEN CODING METHOD . . . | | | |
| DIAGNOSES | | | | | |
| | | DIAGNOSIS CODING METHOD: | | ICD-9 | |
| | | | | | |
| | | DIAGNOSIS CODE - DG1: | | 844.2 | |
| | | DIAGNOSIS DESCRIPTION . . . | | | |
| PROCEDURES | | | | | |
| | | PROCEDURE CODING METHOD . . . | | | |
| PROBLEMS | | | | | |
| | | ACTION CODE . . . | | | |
| MEDICATION ADMINISTRATIONS | | | | | |
| | | NDC CODE: 66267-001 | | | |
| | | QUANTITY: | 30 | | |
| | | QUANTITY UNIT CODE . . . | | | |
| IMMUNIZATIONS | | | | | |
| | | CVX CODE . . . | | | |
| | | | | | |

FIG. 4.

| CLINICAL EVENT DETAILS | | | | | |
|---|---|---|---|---|---|
| | PERSON IDENTIFICATION | | | | |
| | | NAME: | JOHNSON, RICHARD, L. | | |
| | | MOTHER'S MAIDEN NAME: | JONES | | |
| | | BIRTH DATE AND TIME . . . | | | |
| | VISIT IDENTIFICATION | | | | |
| | | IDENTIFIER: | 12345 | | |
| | | ADMIT REASON: | KNEE ARTHROSCOPY | | |
| | | CLASS CODE . . . | | | |
| | ALLERGIES | | | | |
| | | ALLERGEN CODING METHOD: | | | |
| | | ALLERGEN TYPE CODE: | A012 - ASPIRIN | | |
| | | ALLERGEN CODE/MNEMONIC/DESCRIPTION . . . | | | |
| | PATIENT ADVERSE REACTIONS | | | | |
| | | ALLERGEN CODING METHOD . . . | | | |
| | DIAGNOSES | | | | |
| | | DIAGNOSIS CODING METHOD: | | ICD-9 | |
| | | DIAGNOSIS CODE - DG1: | | 844.2 | |
| | | DIAGNOSIS DESCRIPTION . . . | | | |
| | PROCEDURES | | | | |
| | | PROCEDURE CODING METHOD . . . | | | |
| | PROBLEMS | | | | |
| | | ACTION CODE . . . | | | |
| | MEDICATION ADMINISTRATIONS | | | | |
| | | NDC CODE: 66267-001 | | | |
| | | QUANTITY: | 30 | | |
| | | QUANTITY UNIT CODE . . . | | | |
| | IMMUNIZATIONS | | | | |
| | | CVX CODE . . . | | | |
| | ORGANIZATION IDENTIFIER | | | | |
| | | PROVIDER: | 1498000 - DR. JOHN SMITH | | |
| | | ORGANIZATION: | 9988000 - STATE GENERAL HOSPITAL | | |

FIG. 5.

| CLINICAL EVENT DETAILS | | | | | |
|---|---|---|---|---|---|
| PERSON IDENTIFICATION | | | | | |
| | NAME: | JOHNSON, RICHARD, L. | | | |
| | MOTHER'S MAIDEN NAME: | JONES | | | |
| | BIRTH DATE AND TIME . . . | | | | |
| VISIT IDENTIFICATION | | | | | |
| | IDENTIFIER: | 12345 | | | |
| | ADMIT REASON: | KNEE ARTHROSCOPY | | | |
| | CLASS CODE . . . | | | | |
| ALLERGIES | | | | | |
| | ALLERGEN CODING METHOD: | | | | |
| | ALLERGEN TYPE CODE: | A012 - ASPIRIN | | | |
| | ALLERGEN CODE/MNEMONIC/DESCRIPTION . . . | | | | |
| PATIENT ADVERSE REACTIONS | | | | | |
| | ALLERGEN CODING METHOD . . . | | | | |
| DIAGNOSES | | | | | |
| | DIAGNOSIS CODING METHOD: | | ICD-9 | | |
| | | | | | |
| | DIAGNOSIS CODE - DG1: | | 844.2 | | |
| | DIAGNOSIS DESCRIPTION . . . | | | | |
| PROCEDURES | | | | | |
| | PROCEDURE CODING METHOD . . . | | | | |
| PROBLEMS | | | | | |
| | ACTION CODE . . . | | | | |
| MEDICATION ADMINISTRATIONS | | | | | |
| | NDC CODE: 66267-001 | | | | |
| | QUANTITY: | 30 | | | |
| | QUANTITY UNIT CODE . . . | | | | |
| IMMUNIZATIONS | | | | | |
| | CVX CODE . . . | | | | |
| ORGANIZATION IDENTIFIER | | | | | |
| | PROVIDER: | 1498000 - DR. JOHN SMITH | | | |
| | ORGANIZATION: 9988000 - STATE GENERAL HOSPITAL | | | | |
| PERSON IDENTIFIER | | | | | |
| | 0267569 - RICHARD L. JOHNSON | | | | |

FIG. 6.

| CLINICAL EVENT DETAILS | | | | | |
|---|---|---|---|---|---|
| | PERSON IDENTIFICATION | | | | |
| | | NAME: | JOHNSON, RICHARD, L. | | |
| | | MOTHER'S MAIDEN NAME: | JONES | | |
| | | BIRTH DATE AND TIME . . . | | | |
| | VISIT IDENTIFICATION | | | | |
| | | IDENTIFIER: | 12345 | | |
| | | ADMIT REASON: | KNEE ARTHROSCOPY | | |
| | | CLASS CODE . . . | | | |
| | ALLERGIES | | | | |
| | | ALLERGEN CODING METHOD: | | | |
| | | ALLERGEN TYPE CODE: | A012 - ASPIRIN | | |
| | | | P323 - PENICILLIN | | |
| | | ALLERGEN CODE/MNEMONIC/DESCRIPTION . . . | | | |
| | PATIENT ADVERSE REACTIONS | | | | |
| | | ALLERGEN CODING METHOD . . . | | | |
| | DIAGNOSES | | | | |
| | | DIAGNOSIS CODING METHOD: | | ICD-9 | |
| | | | | | |
| | | DIAGNOSIS CODE - DG1: | | 844.2 | |
| | | | | 844.1 | |
| | | DIAGNOSIS DESCRIPTION . . . | | | |
| | PROCEDURES | | | | |
| | | PROCEDURE CODING METHOD . . . | | | |
| | PROBLEMS | | | | |
| | | ACTION CODE . . . | | | |
| | MEDICATION ADMINISTRATIONS | | | | |
| | | NDC CODE: 66267-001 | | | |
| | | QUANTITY: | 30 | | |
| | | QUANTITY UNIT CODE . . . | | | |
| | IMMUNIZATIONS | | | | |
| | | CVX CODE . . . | | | |
| | ORGANIZATION IDENTIFIER | | | | |
| | | PROVIDER: | 1498000 - DR. JOHN SMITH | | |
| | | ORGANIZATION: | 9988000 - STATE GENERAL HOSPITAL | | |
| | PERSON IDENTIFIER | | | | |
| | | 0267569 - RICHARD L. JOHNSON | | | |

FIG. 7.

| CLINICAL EVENT DETAILS | | | | | |
|---|---|---|---|---|---|
| | PERSON IDENTIFICATION | | | | |
| | | NAME: | JOHNSON, RICHARD, L. | | |
| | | MOTHER'S MAIDEN NAME: | JONES | | |
| | | BIRTH DATE AND TIME . . . | | | |
| | VISIT IDENTIFICATION | | | | |
| | | IDENTIFIER: | 12345 | | |
| | | ADMIT REASON: | KNEE ARTHROSCOPY | | |
| | | CLASS CODE . . . | | | |
| | ALLERGIES | | | | |
| | | ALLERGEN CODING METHOD: | | | |
| | | ALLERGEN TYPE CODE: | A012 - ASPIRIN | | |
| | | | P323 - PENICILLIN | | |
| | | ALLERGEN CODE/MNEMONIC/DESCRIPTION . . . | | | |
| | PATIENT ADVERSE REACTIONS | | | | |
| | | ALLERGEN CODING METHOD . . . | | | |
| | DIAGNOSES | | | | |
| | | DIAGNOSIS CODING METHOD: | | ICD-9 | |
| | | | | | |
| | | DIAGNOSIS CODE - DG1: | | 844.2 | |
| | | | | 844.1 | |
| | | DIAGNOSIS DESCRIPTION . . . | | | |
| | PROCEDURES | | | | |
| | | PROCEDURE CODING METHOD . . . | | | |
| | PROBLEMS | | | | |
| | | ACTION CODE . . . | | | |
| | MEDICATION ADMINISTRATIONS | | | | |
| | | NDC CODE: | 66267-001 | | |
| | | QUANTITY: | 30 | | |
| | | QUANTITY UNIT CODE . . . | | | |
| | IMMUNIZATIONS | | | | |
| | | CVX CODE . . . | | | |
| | ORGANIZATION IDENTIFIER | | | | |
| | | PROVIDER: | 1498000 - DR. JOHN SMITH | | |
| | | ORGANIZATION: | 9988000 - STATE GENERAL HOSPITAL | | |
| | PERSON IDENTIFIER | | | | |
| | | 0267569 - RICHARD L. JOHNSON | | | |
| | OUTCOMES CRITERIA | | | | |
| | | CLINICAL | | | |
| | | | MORTALITY | | |
| | | | MORBIDITY . . . | | |
| | | SUBJECTIVE | | | |
| | | | PATIENT SATISFACTION... | | |
| | | CLINICAL/ADMINISTRATIVE | | | |
| | | | LOS – 3.7 DAYS | | |
| | | | QOL | | |

FIG. 8.

COMPUTERIZED SYSTEM AND METHODS FOR GENERATING AND PROCESSING INTEGRATED TRANSACTIONS FOR HEALTHCARE SERVICES

CROSS-REFERENCE TO RELATED APPLICATIONS

This application claims the benefit of U.S. Provisional Patent Application Ser. No. 60/651,503 filed Jan. 6, 2005, entitled "Computerized System and Methods for Generating and Processing Integrated Transactions for Healthcare Services," which is assigned or under obligation of assignment to the same entity as this application, and incorporated in this application by reference.

STATEMENT REGARDING FEDERALLY SPONSORED RESEARCH OR DEVELOPMENT

Not applicable.

FIELD OF THE INVENTION

Embodiments of this invention relate to the field of healthcare information technology systems. More particularly, embodiments of the invention are directed to a system and methods for generating and processing an integrated transaction for supporting the provision of, and adjudication and reimbursement for, healthcare services.

BACKGROUND OF THE INVENTION

While providing the highest level of care in the world, the United States healthcare system is extremely costly. Nearly $1.7 trillion, or roughly 14% of the gross domestic product, is currently spent on healthcare. An unacceptable portion of the costs within the United States healthcare system is attributable to administrative costs. A recent study found that 31% of the overall healthcare expenditures are directed to administrative costs.

The apparent excess in administrative costs is due to a number of reasons. For example, the provision of health care has predominantly been practiced in a paper-based environment. Claims administration, adjudication, reimbursement, benefits management and other administrative, operational and financial processes have also predominantly been conducted in an inefficient, paper-based environment. These paper-based systems are plagued by error, redundancy and friction among the stakeholders within the healthcare system.

The opportunity exists for information technology to be more widely employed to automate, improve and integrate clinical and administrative processes and to connect stakeholders in the healthcare system. To this point, various clinical and administrative information technology systems have been used successful in their respective environments. From a clinical perspective, electronic medical records (EMRs) have been used to structure and store patient information in a comprehensive, longitudinal manner so that relevant information is accessible to care providers at the appropriate time and place. The EMR and other clinical healthcare information technology (HCIT) solutions reduce the number of errors associated with providing care, and minimize the time and effort required to document and retrieve details of the care provided. Other benefits are widely known in the art. From an administrative perspective, on-line claims submittal and electronic fund transfer (EFT) technologies have improved some aspects of the payment and reimbursement process. However, these systems have not been successfully married or connected to one another, and the central component of these administrative systems, the benefit claim, does not include the information required to fairly and efficiently reimburse providers for healthcare services.

In existing systems, the claim in a paper or electronic form is forwarded by the healthcare provider, medical facility or the patient to a payer for processing and payment. Once the claim arrives at the payer, the process of adjudicating the benefit claim begins in accordance with the constraints of the relevant policy and benefit plan contract, and any agreements between the payer and the healthcare provider or facility or organization at which services were rendered. The adjudication of a submitted claim is a process initiated by the payer to determine the health benefits covered under the benefit plan contract, including its limitations, exclusions, schedule of benefit or reimbursement, managed care provisions or any other entitlements or lack of entitlements. The payer adjudication system analyzes the data submitted via the claim and determines whether the claim should be paid, in whole or in part, or be denied.

Once the claim is adjudicated by the payer, an explanation of benefits (EOB) statement is generated. The EOB identifies the services that were billed, the amounts paid to the provider and any reasons for nonpayment. Once returned to the healthcare provider, the EOB is manually reviewed and the codes for any unpaid, underpaid or remarks are compared to those codes of the originally submitted claim. Once the EOB is reviewed and any issues identified, the healthcare provider attempts to correct, revise and resubmit the claim. In this step, incorrect codes or non-applicable codes are corrected, incorrect descriptions of procedures are revised, and the claim is resubmitted to the payer. The healthcare provider then engages the payer to resolve any disputed claim issues and further correct or modify the resubmitted claim. The process may be repeated until all claims have been paid or otherwise resolved.

The existing processes for claim submission and adjudication are labor intensive, time consuming, and provide little assurance that a claim will be paid. The processes largely ignore the core clinical data and information related to the care provided and focus almost exclusively on the billing codes that summarize the care provided. The processes do not account for the condition of the particular patient, the quality of the care provided or the appropriateness of the care provided given the particular clinical circumstances surrounding the patient and the encounter. As such, the standards of review are based on generalities rather than the scientifically supported evidence regarding the provision of appropriate, high quality care. These problems are compounded since the information technology systems for providing care do not interoperate with the systems for reimbursement.

As noted briefly above, a minimal level of information technology has been employed in the claims adjudication process. For example, some administrative systems allow providers to submit claims electronically. Also, benefits companies provide online access for verifying eligibility and plan coverage, and determining the status of claims and other benefit information. Other existing systems address claims processing from a multi-system perspective, and are plagued by interfaces, incompatibilities and limited functionality. By way of example, one software application may be used to edit a claim while another software application determines eligibility and yet another software application addresses revenue management. In these and other examples, significant user intervention is required to adjudicate and reimburse the care provider after a claim is produced, which also leads to inefficiencies and increased administrative costs. Little of the friction inherent in the manual systems is eliminated by these computerized systems. The clinical information for which the claim is submitted is sparse, incomplete and largely ignored. As such, the existing systems are unable to adjudicate and reimburse for care in an efficient, time-saving and cost-effective way. As a result, the cost of providing care and the administration of care has skyrocketed in spite of increased efficiencies that information technology has provided in particular domains.

There is a need for a system and methods that integrate clinical, financial and payer benefits information and provide a common process for the provision of care and administration of healthcare benefits to reduce the medical error and eliminate the variance, waste, delay and friction in the current healthcare system. There is also a need for a trusted and open automated system accessible by the person receiving care, the provider and the payers. There is a further need to introduce medically supported evidence in the process of providing and paying for care to improve the level of care, and allow providers to employ the best medicine while receiving the appropriate level of reimbursement for the care provided. The system and methods of the present invention address these needs and others evident from the description provided below.

SUMMARY OF THE INVENTION

The invention overcoming these and other problems in the art relates in one regard to a system and methods for processing an integrated transaction for efficient provision of healthcare, and adjudication and reimbursement for the care provided. In embodiments, a method for adjudicating and reimbursing a care provider for services provided for a clinical event is provided. The method includes the step of receiving a transaction having a number of clinical data elements. The method also includes the steps of accessing a data store including payer information and determining whether the transaction is eligible for reimbursement by the payer. The method also includes the steps of accessing a first knowledge base comprising evidence-based standards for providing medically appropriate care and selectively performing analysis of the clinical data elements of the transaction against at least one standard to determine if the care provided is medically appropriate. The method further includes the steps of accessing a second knowledge base containing at least one criterion for assessing the quality of care provided and selectively performing analysis of the clinical data elements of the transaction against the at least one criterion to determine if the care provided is medically appropriate. Also, the method includes determining a level of reimbursement based on the medical appropriateness and quality of the care provided and authorizing reimbursement of the care provider from at least one payer.

BRIEF DESCRIPTION OF THE DRAWINGS

The present invention is described in detail below with reference to the attached drawing figures, wherein:

FIG. 4 illustrates the initial clinical event details of the integrated transaction in accordance with an embodiment of the invention;

FIG. 5 illustrates the integrated transaction of FIG. 4 aggregated to include an organization identifier in accordance with an embodiment of the invention;

FIG. 6 illustrates the integrated transaction of FIG. 5 aggregated to include a person identifier in accordance with an embodiment of the invention;

FIG. 7 illustrates the integrated transaction of FIG. 6 aggregated to include EHR data elements in accordance with an embodiment of the invention;

FIG. 8 illustrates the integrated transaction of FIG. 7 aggregated to include data elements used to determine the quality of the care provided in accordance with an embodiment of the invention;

DETAILED DESCRIPTION OF EMBODIMENTS

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides a computerized system and methods for use in generating and processing an integrated transaction for supporting the provision of, and reimbursement for, healthcare services. An exemplary operating environment for the present invention is described below.

Figure 1:
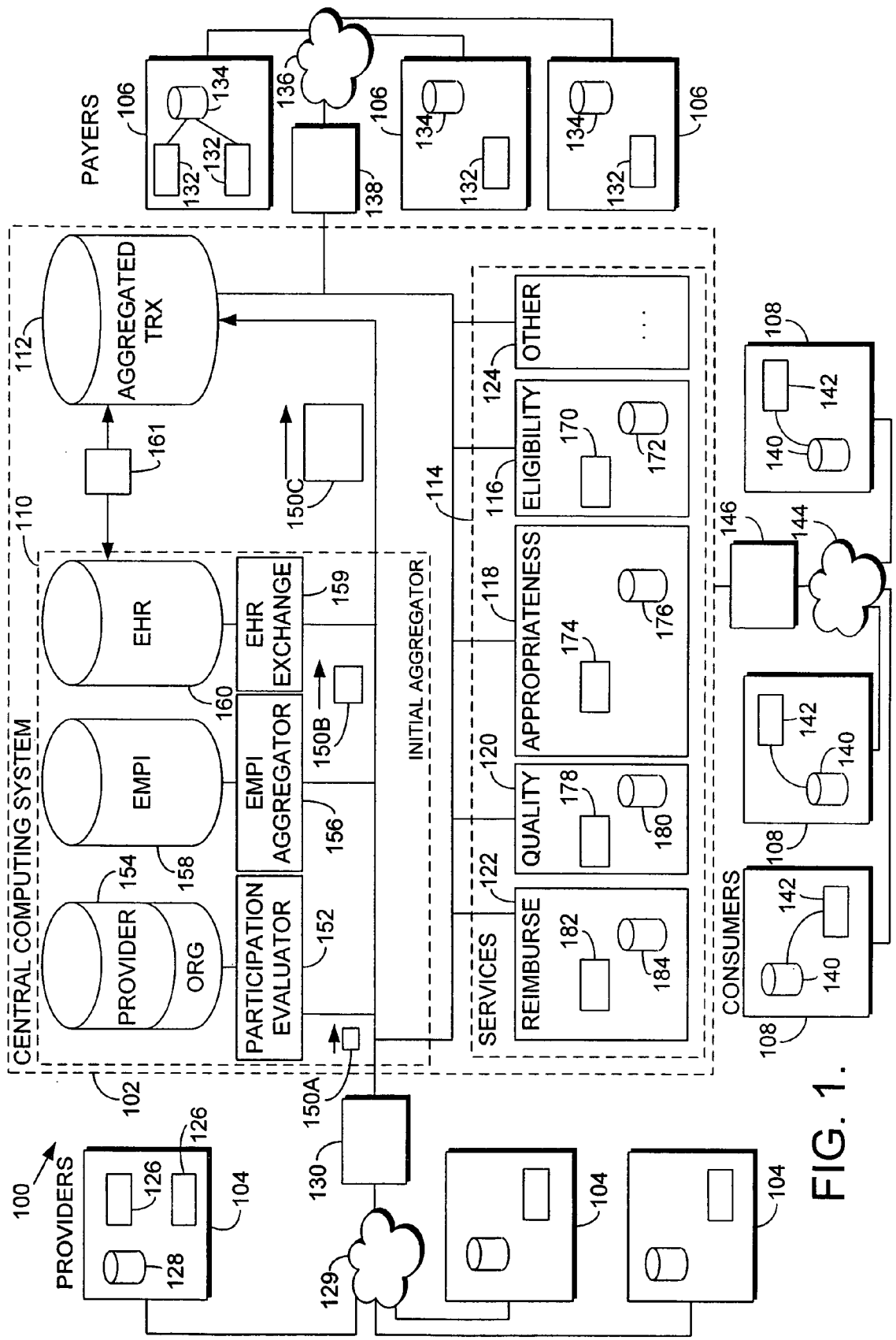
FIG. 1 is a block diagram of an exemplary computing environment for use in implementing the present invention.

Referring to the drawings in general, and initially to FIG. 1 in particular, an exemplary computing system environment, for instance, a medical information computing system, on which the present inventions may be implemented is illustrated and designated generally as reference numeral 100. It will be understood and appreciated by those of ordinary skill in the art that the illustrated medical information computing system 100 is merely an example of one suitable computing environment and is not intended to suggest any limitation as to the scope of use or functionality of the invention. Neither should the medical information computing system 100 be interpreted as having any dependency or requirement relating to any single component or combination of components illustrated therein.

The system 100 includes a central computing system 102 communicating with one or more care provider locations 104, payers 106 and healthcare consumers 108. As described below in greater detail with reference to FIGS. 3-8, central computing system 102 includes an initial transaction aggregator 110 for receipt and accumulation of clinical, financial and administrative data elements. Each integrated transaction is stored within a data store 112 containing a number of transactions for processing in accordance with embodiments of the invention.

As described below with reference to FIGS. 9-12, the central computing system further includes a services component 114 for automatically adjudicating each integrated transaction. Services component 114 includes an eligibility module 116, an appropriateness module 118 and a quality module 120. Services component 114 also includes a reimbursement module 122 for automatically reimbursing, or initiating the reimbursement of, the care provider in real time (or near real time) from one or more payers though the central computing system. Services component 114 also includes additional modules 124 capable of processing the integrated transactions for purposes in addition to the services provided by modules 116, 118, 120 and 122.

Healthcare services are provided at any of a number of care provider locations 104. These locations can be located at medical environments, for example, but not limited to, hospitals, other inpatient settings, pharmacies, a clinician's office, ambulatory settings, testing labs and a person's home environment. In an embodiment, one or more computing devices 126 are located at, or associated with, each care provider location 104 and receive clinical, financial and administrative data elements for storage at one or more data stores 128 located at, or associated with, each care provider location. For example, the computing devices 126 and data stores 128 may be physically located at the provider's physical locations, at remote locations at which the health care information technology systems are hosted for the providers, or distributed there between. The computing devices 126 communicate with the central computing system 102 through a network 129 and an interface 130.

The data elements such as those received at the providers 104 may include, for example, a variety of clinical, financial and administrative data elements as described in embodiments of the invention with reference to FIGS. 4-8. Clinical data elements include "clinical event details" submitted by the provider for the care provided and "EHR data elements" that pre-exist the submission of the particular transaction being adjudicated and are stored in the system as described below. For example, clinical data elements include, for example, patient identification data, diagnosis data, patient morbidity, mortality and recovery rates, drug prescription and other drug delivery and management information, and data elements traditionally captured at the point of care or during the care process and stored in an electronic medical record (EMR). Financial and administrative data elements may include hospital or other occupancy data, supply information, medical staff information, scheduling information, or other types of information related to clinical operations.

Payers 106 are similarly connected to the central computing system 102 of the present invention. Payers 106 include without limitation, employers, government entities (such as the Centers for Medicare and Medicaid Services), charities, insurers and secondary insurers. In embodiments, one or more computing devices 132 associated with each payer 106 collect and manage payer data elements that are stored in one or more data stores 134. The payer data elements include, without limitation, procedure codes, physician identification, insurance or other coverage data including co-pay and deductible amounts, eligibility requirements, and benefit reimbursement levels. The computing devices 132 communicate with the central computer system 102 through a network 136 and an interface 138.

Consumers 108 are also connected to the central computing system 102. Consumers 108 include individuals receiving care and individuals responsible for the care of others. For purposes of the present invention, consumers may also include any of a number of other entities such as financial institutions responsible for an aspect of a consumer obligation. A number of computing devices 142 associated with the consumers collect clinical, financial and administrative data elements stored in one or more data stores 140. The computing devices 142 communicate with central computer system 102 through a network 144 and an interface 146.

The computing devices at the provider and payer institutions and the central computing system are preferably general purpose computing devices having a server. Components of the servers may include, but are not limited to, a processing unit, internal system memory, and a suitable system bus for coupling various system components, including associated data stores. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The servers typically include therein or have access to a variety of computer readable media, for instance, at the associated data stores and knowledge bases. Computer readable media can be any available media that can be accessed by the servers, and includes both volatile and nonvolatile media, removable and nonremovable media. By way of example, and not limitation, computer readable media may comprise computer storage media and communication media. Computer storage media include volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by a server. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

Servers may operate in a computer network using logical connections to other general computing devices. Other general computing devices may be a personal computer, router, a network PC, a peer device or other common network node, and may include some or all of the elements described above relative to server. The consumer computing devices 142 will typically consist of personal computers integrated with data store 140.

A user may enter commands and information into the general computing devices through input devices, such as keyboards, pointing devices, commonly referred to as a mouse, trackball, or touch pad. Other input devices may include a microphone, satellite dish, scanner, or the like. The computing devices may have any sort of display device, for instance, a monitor. In addition to a monitor, the computing devices may also include other peripheral output devices, such as speakers and printers.

Although many other internal components of server and general computing devices are not shown, those of ordinary skill in the art will appreciate that such components and their interconnection are well known. Accordingly, additional details concerning the internal construction of the server and other computing devices need not be disclosed in connection with the present invention.

Data elements are communicated between the providers, payers and consumers and the central computing system through networks 129, 136 and 144, for instance, via a local area network (LAN) and/or a wide area network (WAN), but may also include other networks. Such networking environments are commonplace in offices, enterprise-wide computer networks, intranets and the Internet. When utilized in a WAN networking environment, servers may include a modem or other means for establishing communications over the WAN, such as the Internet. In a networked environment, program modules or portions thereof may be stored in server, or data stores, or on any of the general computing devices such as the remote computers. For example, and not limitation, various application programs may reside on the memory associated with any one or all of the computing devices. It will be appreciated that the network connections shown are exemplary and other means of establishing a communications link between the computers may be used.

The data stores provide storage of computer readable instructions, data structures, program modules, and other data for the computing devices. As described herein, the data stores may include, for instance, a query engine such as a SQL engine or other resources to facilitate the maintenance, interrogation and transmission of the data. The data stores may be or include a large-scale or other database hosting facility, such as a site including or interfacing to, for example, relational databases such as the Oracle™ relational database sold commercially by Oracle Corp. or others. Other storage or query formats, platforms or resources such as OLAP (On Line Analytical Processing), SQL, storage area networks (SANs), redundant arrays of independent disks (RAID) or others may also be used, incorporated or accessed by data stores, which may be supported by servers or other resources. In embodiments, the invention contemplates a distributed transaction having a number of pointers to the data elements comprising the transaction.

The methods and system of the invention receives data, and provides information to adjudicate and reimburse for care provided in response to relevant input and/or actions initiated within the healthcare system. Although the method and system are described as being implemented in a WINDOWS operating system operating in conjunction with a comprehensive healthcare network, one skilled in the art would recognize that the method and system can be implemented in any system supporting the receipt and processing of the relevant data elements and inputs.

Figure 2:
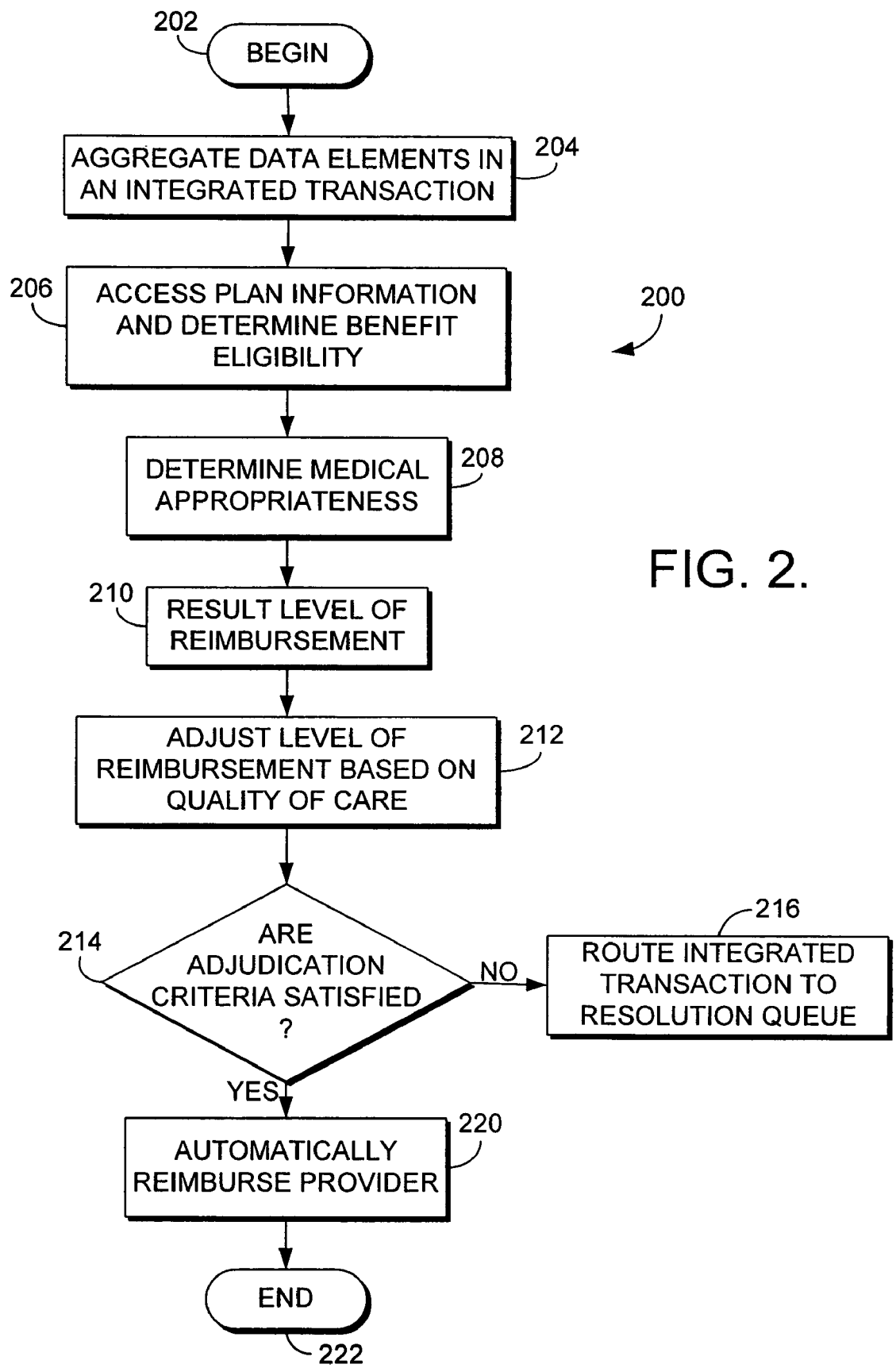
FIG. 2 is a flow chart representative of an exemplary computer program for generating and processing an integrated transaction to reimburse a care provider for a clinical event in accordance with an embodiment of the invention.

An exemplary method 200 for generating and processing an integrated transaction to reimburse a care provider is illustrated in the flow diagram of FIG. 2. Initially, at block 202, the method is initiated. Subsequently, at block 204, the data elements (including the clinical event details) are combined with traditional administrative and financial details and aggregated to form initially an integrated transaction as described below with reference to FIGS. 3-8.

Figure 3:
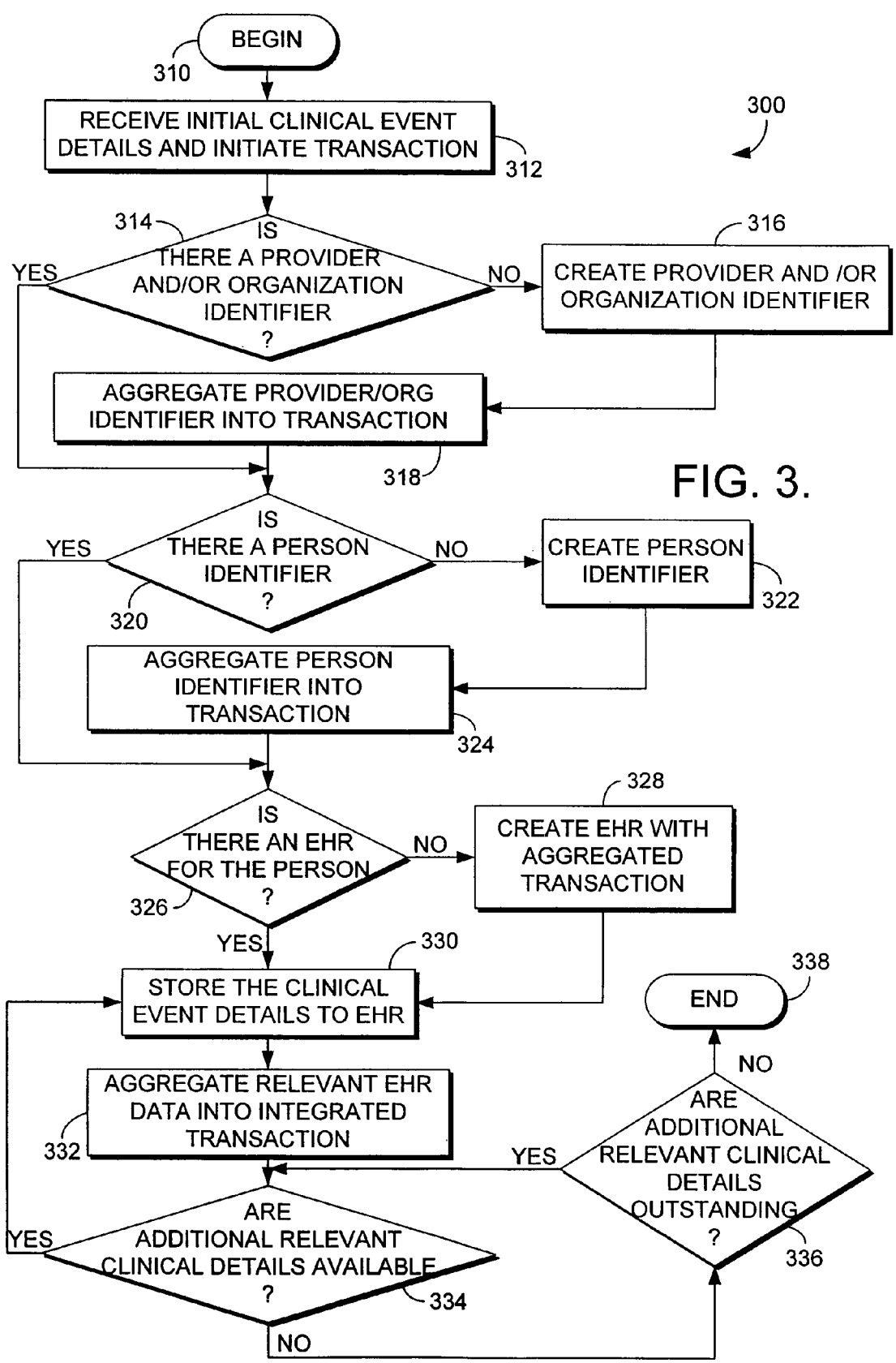
FIG. 3 is a flow chart representative of an exemplary computer program for creating the integrated transaction and building the integrated transaction of FIG. 2 in accordance with an embodiment of the invention.
Figure 9:
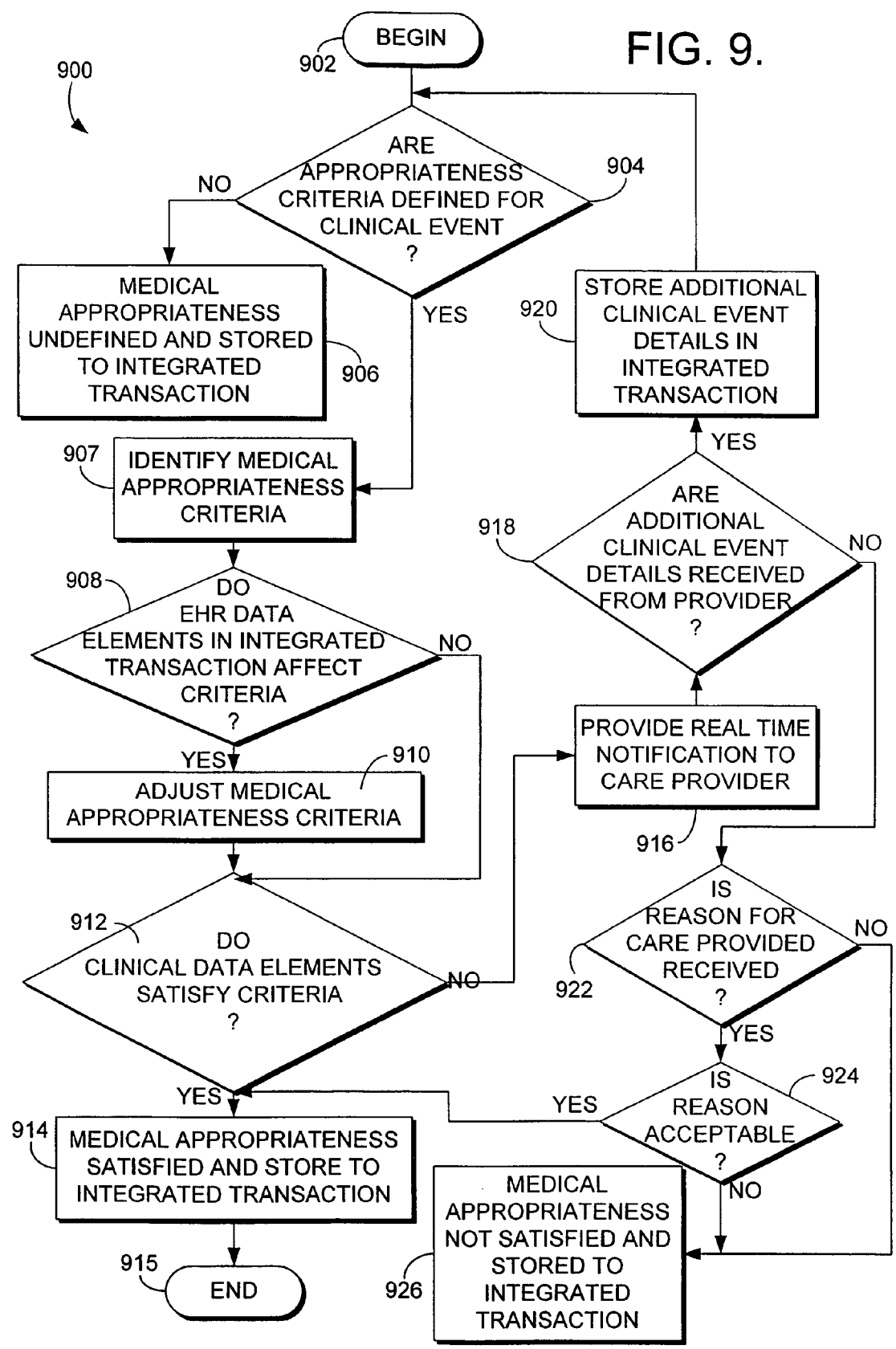
FIG. 9 is a flow chart representative of an exemplary computer program for adjudicating the integrated transaction based on the medical appropriateness of the care provided during the clinical event in accordance with an embodiment of the invention.

An exemplary method 300 for creating and building an integrated transaction is illustrated in the flow diagram of FIG. 3. The method begins at block 310. Next, at block 312, the system receives initial clinical event details (and traditional administrative and financial details) to initiate the transaction. In an embodiment, the clinical event details are captured by the care provider at the point of care. For example, a number of structured care templates may be used to capture contemporaneous or near-contemporaneous clinical data elements such as laboratory test results, assessments, imaging studies, pharmaceutical prescription or use, clinical outcomes or other data as set forth with specificity below. That data may be captured and stored into a documented care note, chart or other record, which may in embodiments be stored to a clinical data store such as data store 128 (FIG. 1), and combined with existing data in the data store 128 of each provider. In this embodiment, when a documented care note is signed and stored within the patient record, the care provider is prompted to add any of a number of clinical event details typically required for completing the processing of the transaction in accordance with the present invention that are not already included in the patient's record.

By way of example, FIG. 4 illustrates a subset of initial clinical event details forming the initial integrated transaction at block 312 of FIG. 3. In an embodiment, the clinical event details include, without limitation, person identification (or person identifier), visit identification, allergies, patient adverse reactions, diagnoses, procedures, problems, medication administrations, and immunizations. The person identification includes a number of elements specific to the individual person receiving care (or "patient"). For example, address, gender, race, communication mechanism list, and marital status for the person are aggregated and included in each integrated transaction.

Visit identification includes those clinical event details specific to the individual person's visit to a care provider (primary care physician, specialist, hospital). For example, visit identification includes clinical event details such as admitting reason, admitting date, discharge, and servicing facility, among others. The clinical event details also include medically related information specific to the person. Information regarding any allergies is aggregated in the transaction. Allergy-related adverse reactions are also collected and included in the integrated transaction.

In addition, clinical event details regarding the clinical diagnoses and the procedures performed, any medications administered, and immunizations given to the patient are included in the integrated transaction. Table 1 includes an exemplary list of clinical event details included in the initial transaction. In this embodiment, a number of the data elements are defined by Health Level 7's (HL7) Continuity of Care Record (CCR).

TABLE 1

Clinical Event Details

Person Identification
    Name
        First
        Middle
        Last
        Suffix
    Mother's Maiden Name
    Birth Date and Time
    Death Date and Time
    Gender Code
    Race Code
    Address List (Home, Business, Etc.)
        Address Type Code
        City
        State/Province
        County Code
        Postal Code
        Country Code
    Communication Mechanism List (Home, Business, email, Etc.)
        Communication Mechanism Type Code
        Communication Mechanism
    Identifier List (Driver's License Number, SSN, MRN, etc.)
        Identifier Type Code
        Identifier
    Primary Language Code
    Marital Status Code
    Religion Code
    Nationality Code
    Citizenship
    Physician List (PCP)
        Physician Relationship Type Code
        Identifier
        First
        Middle
        Last
        Suffix
Visit Identification
    Identifier
    Class Code
    Type Code
    Admit Reason
    Admit Date/Time
    Discharge Date/Time
    Physician List (Admitting, Attending, Referring, Consulting, etc.)
        Physician Relationship Type Code
        Identifier
        First
        Middle
        Last
        Suffix
    Servicing Facility
        City
        State/Province
        County Code
        Postal Code
        Country Code
    Estimated Length of Inpatient Stay
    Actual Length of Inpatient Stay
Allergies
    Allergen Coding Method
    Allergen Type Code
    Allergen Code/Mnemonic/Description
    Allergy Severity Code
    Allergy Reaction Code
    Identification Date
Patient Adverse Reactions
    Allergen Coding Method
    Allergen Type Code
    Allergen Code/Mnemonic/Description
    Allergy Severity Code
    Allergy Reaction Code
    Allergy Action Code
    Allergy Unique Identifier
    Action Reason
    Sensitivity to Causative Agent Code
    Allergen Group Code/Mnemonic/Description
    Onset Date

TABLE 1-continued

Clinical Event Details

Onset Date Text
    Reported Date/Time
    Reported By
    Relationship to Patient Code
    Alert Device Code
    Allergy Clinical Status Code
    Statused by Person
    Statused by Organization
    Statused at Date/Time
Diagnoses
    Diagnosis Coding Method
    Diagnosis Code - DG1
    Diagnosis Description
    Diagnosis Date/Time
    Diagnosis Type
    Major Diagnostic Category
    Diagnostic Related Group
    DRG Approval Indicator
    DRG Grouper Review Code
    Outlier Type
    Outlier Days
    Outlier Cost
    Grouper Version And Type
    Diagnosis Priority
    Diagnosing Clinician
    Diagnosis Classification
    Confidential Indicator
    Attestation Date/Time
    Diagnosis Identifier
    Diagnosis Action Code
Procedures
    Procedure Coding Method
    Procedure Code
    Procedure Description
    Procedure Date/Time
    Procedure Functional Type
    Procedure Minutes
    Anesthesiologist
    Anesthesia Code
    Anesthesia Minutes
    Surgeon
    Procedure Practitioner
    Consent Code
    Procedure Priority
    Associated Diagnosis Code
    Procedure Code Modifier
    Procedure DRG Type
    Tissue Type Code
    Procedure Identifier
    Procedure Action Code
Problems
    Action Code
    Action Date/Time
    Problem ID
    Problem Instance ID
    Episode of Care ID
    Problem List Priority
    Problem Established Date/Time
    Anticipated Problem Resolution Date/Time
    Actual Problem Resolution Date/Time
    Problem Classification
    Problem Management Discipline
    Problem Persistence
    Problem Confirmation Status
    Problem Life Cycle Status
    Problem Life Cycle Status Date/Time
    Problem Date of Onset
    Problem Onset Text
    Problem Ranking
    Certainty of Problem
    Probability of Problem (0–1)
    Individual Awareness of Problem
    Problem Prognosis
    Individual Awareness of Prognosis
    Family/Significant Other Awareness of Problem/Prognosis
    Security/Sensitivity
Medication Administrations

TABLE 1-continued

Clinical Event Details

NDC Code
Quantity
Quantity Unit Code
Dose
Strength
Strength Unit Code
Interval
Route Code
Date and Time
Provider
    Identifier
    First
    Middle
    Last
    Suffix
Immunizations
    CVX Code
    Quantity
    Quantity Unit Code
    Dose
    Strength
    Strength Unit Code
    Interval
    Route Code
    Start Date and Time
    End Date and Time
    Provider
        Identifier
        First
        Middle
        Last
        Suffix The clinical event details are aggregated with administrative and financial data associated with traditional claims and submitted to the central computer system 102 by the care provider 104 through network 129 and interface 130. Interface 130 may reside within the central computing system or externally to the system as illustrated in FIG. 1. In an embodiment, the interface places the data elements received from the providers in a standard format capable of processing by the services component 114 of the central computing system. In embodiments, the transaction is defined in a standard format such as the CCR and employed by all providers accessing the system. Alternatively, conditioning engines may be employed to translate transactions of differing formats into a standard format for processing in accordance with the invention. Once the initial set of data elements are received and structured to the standard format, an initial transaction 150A is defined as shown in FIG. 1.

With reference back to FIG. 3, once the integrated transaction 150A is defined, the system determines at block 314 if there is a unique identifier for the provider of services and/or the organization at which services were rendered as identified in the integrated transaction. As illustrated in FIG. 1, initial transaction aggregator 110 includes a participation evaluator 152 and a data store 154 containing unique identifiers for providers and organizations known to the central computing system 102. The participation evaluator 152 determines if the provider is a known provider, and if the organization is a known organization, by querying the data store 154. Known providers and organizations include providers and organizations associated with a benefit plan of one of the payers 106 (as provided to the central system through network 136 and interface 138). Providers and organizations that have previously submitted transactions also have unique identifiers in the data store 154.

With reference back to FIG. 3, if either the provider or the organization does not have a unique identifier, then a new identifier is created at block 316. Next, the new identifier is aggregated into the integrated transaction at block 318. If unique identifiers are found in the data store 154 at block 314, then block 318 is bypassed. By way of example, FIG. 5 illustrates an integrated transaction including a provider identifier and an organization identifier as included in the integrated transaction. The provider identifier for fictitious physician John Smith is 1498000 and the organization identifier for fictitious organization State General Hospital is 9988000. Each identifier is stored in data store 154 and included in the integrated transaction related to the care provided under the heading entitled Organization Identifier.

Initial aggregator 110 also includes an enterprise master person index (EMPI) aggregator 156 and a data store 158 containing unique identifiers for persons receiving care or otherwise accessing the system. At block 320, the EMPI aggregator determines if a unique person identifier is stored in data store 158 for the patient identified in the integrated transaction. A person identifier, using enterprise master person index (EMPI) technology known to those of ordinary skill in the art, is established for the person and does not change throughout the lifetime of the person. Known people include people participating in a benefit plan of one of the payers 106. Other people that have previously submitted transactions to, or otherwise accessed services provided by, the central computing system 102, have unique identifiers in the data store 154. By way of example, FIG. 6 illustrates the integrated transaction (150B in FIG. 1) including a person identifier. Specifically, in this instance, the person identifier for fictitious person Richard L. Johnson is 0267569 in the integrated transaction.

With reference back to FIG. 3, if the person receiving care does not have a unique identifier as determined at block 320, a new identifier is created at block 322. Next, the new identifier is aggregated into the integrated transaction at block 324. If a unique identifier exists at block 320, then block 324 is bypassed.

The initial aggregator 110 also includes an electronic health record (EHR) exchange 159 and an EHR data store 160 containing centralized health records for persons interacting with the central computing system 102. At block 326, the EHR exchange 159 determines if an electronic health record exists in the EHR data store for the person identified in the integrated transaction. If an existing EHR is present, then the integrated transaction is stored to the EHR at block 328. If an EHR is not located in the EHR data store 160, then an EHR is created at block 328 based on the clinical event details of the integrated transaction. Next, at block 330, the system stores the clinical event details to the EHR data store 160.

Next, at block 332, EHR data elements from the EHR data store are aggregated into the integrated transaction. As discussed below, historical EHR data elements may affect the appropriateness and quality determinations made by services component 114, and ultimately the amount of reimbursement for the care provided. These EHR data elements are aggregated into the integrated transaction for further processing. By way of example, FIG. 7 illustrates the integrated transaction (150C of FIG. 1) including an allergy retrieved from the EHR data store 160. Specifically, in this instance, the penicillin allergy of the patient is present in the EHR (due to prior transaction or receipt of the allergy from an electronic medical record or other input) but not the initial integrated transaction. The penicillin allergy is aggregated under the Allergies heading (to accompany aspirin). The penicillin allergy may be relevant to the adjudication of appropriateness of patient care and is thus included in the integrated transaction.

In embodiments, an EHR may be formed for each person interacting with the system 100 by storing the incremental data elements received with each transaction. Also, care providers may submit integrated transactions for those clinical events for which reimbursement is not requested so that the clinical event details can be stored in the EHR data store 160. For example, transactions for cosmetic surgery and other types of care paid for by the person receiving care can be added. Also, consumers, care providers and payers may provide information to their EHR and have access to the history through the system of the present invention as, for example, through an EHR viewer module provided by services component 114.

Accordingly, the EHR data store 160 may serve as a robust community EHR. The financial incentive of providers to receive reimbursement provides the requisite incentive for the providers to submit an integrated transaction. By associating each integrated transaction with a unique person identifier and storing the transaction together, an EHR is formed. When several large payer populations are managed with the system, the EHR data store results in a community EHR. In embodiments, logic may be employed for controlling updates to the EHR based on a number of factors such as continuity of submitting provider, timing, method for data capture and the like. In other embodiments, audit trails for updates may be provided. In other embodiments, feedback may be provided by the system when inconsistent data is being submitted than data in the EHR.

Returning to FIG. 3, at block 334, the system determines if additional, relevant clinical event details are available from one or more providers. Some data elements required to complete adjudication may not be available at the time of care. For example, outcomes and results data required to determine the quality of the care provided are oftentimes not available when the initial transaction is initiated. By way of example, FIG. 8 illustrates the integrated transaction of FIG. 7 aggregated to include a length of stay of 3.7 days. In this instance, the length of stay may be a relevant indicator of the quality of care provided as described below with reference to FIGS. 10 and 11.

Table 2 includes an exemplary list of clinical event details related to outcomes (or results) of the care provided as may be aggregated at step 332.

TABLE 2

| Observations (Results) |
|---|
| Identifier |
| Value Type Code |
| Value |
| Units Code |
| Reference Range |
| Abnormal Code List |
|     Abnormal Code |
| Result Status |
| Reference Range Effective Date |
| Date and Time |
| Producer |
|     Identifier |
|     Identifier Type Code |
|     First |
|     Middle |
|     Last |
| Responsible Observer |
|     Identifier |
|     Identifier Type Code |
|     First |

TABLE 2-continued

| Observations (Results) |
|---|
|     Middle |
|     Last |
| Method |
| Date/Time of the Analysis |

With reference back to FIG. 3, if additional clinical details are not available at block 336, the system determines if any additional relevant clinical details that may affect adjudication and reimbursement are outstanding. In some cases, certain details are required for adjudication and reimbursement of the care provided. In other cases, as described below with respect to FIG. 9, a care provider documents additional clinical event details for the integrated transaction after the initial submission to demonstrate that the appropriate care was provided. For example, a provider may input a justified reason for departing from the generally accepted protocol for medically appropriate care. The system may similarly query the provider for submission of such justification at block 334. If received, the system stores the justification in the EHR at block 330 and aggregates the reason as an additional clinical data element in the integrated transaction at block 332.

Some clinical event details are less relevant to adjudication, and processing of the integrated transaction may be completed in the absence of these details. For example, additional EHR data elements that impact the standards for medical appropriateness in rare cases may not required, and the omission of these EHR data elements may not halt adjudication and reimbursement for care. If no additional clinical event details are outstanding or the outstanding clinical event details would not halt processing of the integrated transaction, the aggregation process of FIG. 2 then ends at block 338.

With reference back to FIG. 2, once the data elements (including clinical event details) are aggregated in the integrated transaction at block 204, the system accesses plan information (or benefit data elements) provided by the payers and determines benefit eligibility. Eligibility module 116 includes an eligibility engine 170 and an eligibility data store 172 containing eligibility information from each of the payers 106. Eligibility engine 170 selectively determines if the care described in the integrated transaction is eligible for reimbursement under any of the payer plans. The determination is made by methods known by those of ordinary skill in the art. Data reflecting this determination is aggregated in the integrated transaction data store 112. If the data is part of the data forming the EHR, a synchronizer 161 updates the EHR data store 160.

Once eligibility is determined at block 206, the medical appropriateness module 118 determines if the care provided is medically appropriate based on the integrated transaction. An exemplary method 900 for adjudicating the integrated transaction based on the medical appropriateness of the care provided is illustrated in the flow diagram of FIG. 9.

Initially, the process begins at block 902. Subsequently, at block 904, the system determines if appropriateness criteria are defined for the clinical event for which reimbursement is sought. In an embodiment, appropriateness module 118 includes an appropriateness engine 174 and an appropriateness knowledge base 176. Guidelines, standards of care and other normative information are contained in knowledge base 176. These may, for instance, include recommended or best practices for different categories of diseases, patients or treatments as well as other clinical baseline or objective data. In embodiments, the knowledge base 176 may include or access clinical guidelines published or released by Zynx Health, Inc. or other content providers. Other sources of objective, evidence or research-based clinical guidelines and standards may be assessed or incorporated, such as for example data published or provided by the Joint Commission on Accreditation of Healthcare Organizations. Other public or private sources or combinations of sources of clinically-related criteria or guidelines may also be used. At block 904, appropriateness engine 174 identifies the relevant clinical data elements in the integrated transaction to select appropriateness criteria from the knowledge base 176. If appropriateness criteria do not exist for the care provided, at block 906, the system determines that the medical appropriateness is incapable of being evaluated and stores the determination in the integrated transaction.

If appropriateness criteria are defined for the clinical event identified in the integrated transaction, the criteria relevant to the integrated transaction are identified at block 907 by the appropriateness engine 174. Next, at block 908, the system determines if EHR data elements aggregated in the integrated transaction affect the relevance criteria identified at block 907. As mentioned above, "EHR data elements" are clinical data elements that pre-exist the initial transmission of the transaction. If EHR data elements affect the medical appropriateness criteria, the medical criteria are adjusted at block 910 as more fully described with reference to an example below.

If the EHR data elements in the integrated transaction do not affect the criteria, or after the EHR data elements in the integrated transaction have been used to adjust the medical appropriateness criteria, the system determines at block 912 whether the clinical data elements in the integrated transaction satisfy the medical appropriateness criteria. If the medical appropriateness criteria are satisfied, the determination is stored to the integrated transaction at block 914 and the adjudication of medical appropriateness ends at block 915.

If, at block 912, the clinical data elements in the integrated transaction do not satisfy the medical appropriateness criteria, the system notifies the care provider at block 916 that one or more of the criteria are unsatisfied. Preferably, the notification is made in real time so that the provider may add additional details regarding the care provided.

Once the care provider is notified that the medical appropriateness criteria have not been satisfied, the system determines if additional clinical event details are received from the care provider at block 918. For example, before submitting the initial transaction, the care provider may have inadvertently neglected to input relevant clinical event details. If additional clinical event details are received, those clinical event details are stored in the integrated transaction at block 920. Then, the process 900 re-initiates at step 904 until a determination of medical appropriateness is made.

If, at block 918, additional clinical event details are not received from the care provider, the care provider is then given the opportunity at block 922 to explain or justify the care provided or omitted. If the system determines that a reason has been received, at block 924, the system then determines if the reason is acceptable. If the reason is deemed acceptable against a pre-defined list of acceptable reasons (stored in the appropriateness knowledge base 170), the reason is aggregated in the integrated transaction and medical appropriateness adjudication is deemed satisfied and stored at block 914 and the determination of medical appropriateness ends at block 915.

If, at block 922, a reason for the care provided is not received, then the system determines that medical appropriateness is not satisfied and the determination is stored to the integrated transaction at block 906. If a reason is received at block 922, but the reason is deemed unacceptable at block 924, the system determines that medical appropriateness remains unsatisfied and stores the determination as part of the integrated transaction at block 926.

In operation, by way of a number of examples, processes for determining medical appropriateness based on the integrated transactions are described herein. In a first example, assume a fictional person requires arrhythmia management. After the integrated transaction is initially aggregated and eligibility determined as described above, medical appropriateness is adjudicated according to the method 900 of FIG. 9. After the process is initiated at block 902, the system determines if appropriateness criteria are defined for the clinical event at block 904. In this example, at block 907, a number of baseline appropriateness criteria are defined for the clinical event, and the system identifies these criteria. In this example, the appropriateness criteria for arrhythmia management indicates that certain medication treatments (including pre-determined doses, ranges, frequencies and forms) are medically appropriate. Next, at block 908, the system determines if EHR data elements in the integrated transaction affect the criteria. In this case, the medical evidence suggests that it is medically appropriate to implant a pacemaker for the purpose of arrhythmia management if the medical history for the patient (as stored in the EHR) include bradycardia (slow heart beat) and syncope (fainting). If the integrated transaction includes these observations or conditions, the medical appropriateness criteria are adjusted to include a pacemaker as an appropriate medical treatment. Next, at block 912, the system determines if the clinical data elements satisfy the criteria. In this case, drug treatment, a pacemaker or the combination of both treatments are appropriate. If one or both of the appropriate sets of clinical data elements (drug treatment or pacemaker) are documented for the care provided, then medical appropriateness is satisfied and stored as part of the integrated transaction at block 914.

In another example, a hypothetical person admits to the Emergency Department (ED) complaining of chest pains and shortness of breath. Upon examination, it is determined that the person is experiencing heart failure and the care process is initiated to treat the person. In this case, a number of baseline appropriateness criteria are defined for the condition, and the system identifies the criteria at block 907. Specifically, the appropriateness criteria require that aspirin be administered within the first twenty-four hours of admission. In this case, assume the care provider did not administer aspirin within the first twenty-four hours of admission, so the medical appropriateness criteria are not satisfied at block 912. Next, at block 916, the care provider is notified in real time that the medical appropriateness criteria have not been satisfied. At block 918, the system determines if additional clinical event details are received from the care provider. In this case, no additional clinical event details are received. Thus, at block 922, the system next determines if a reason for the departing from the medially appropriate care has been received. In this case, the provider documents that the person had taken aspirin at home minutes before presenting at the ED, therefore, a second dose of aspirin would have been inappropriate. Accordingly, at block 924, the system determines that the reason is acceptable. Medical appropriateness is satisfied and stored to the integrated transaction at block 914.

In another example, reference is made to a genetic test called SHOX-DNA-Dx developed by Esoterix with a license from Eli Lilly & Company. This text detects mutations and deletions in the SHOX (Short Stature Homeobox) gene which is believed to cause short stature. Blaschke R. J. & Rappold G.

A. *SHOX: Growth, Leir-Weill and Turner syndromes.* (Review) TEM 11, 227-230. This test was first discovered in 1997. In this example, a clinician such as an endocrinologist would order this new genetic test to diagnosis a child with short stature rather than the conventional and expensive testing processes. However, when the SHOX-DNA-Dx test is first introduced, the knowledge base 176 of appropriateness module 118 would not include the test as medically appropriate to determine whether a person has short stature.

As such, in this fictional example, at blocks 904 and 907, the system would identify that the appropriate care is to order the convention tests for patients of a certain height and weight. Next, at block 908, the system would determine if EHR data elements in the integrated transaction affect the appropriateness criteria. In this example, clinical data elements that could affect whether testing is appropriate include criteria defining heights and ages of the person's family members. These data elements may indicate that the likelihood of short stature is relatively high or low in combination with the patient's height and weight, and the medical appropriateness criteria may be adjusted at block 910 to allow for testing or disallow for testing.

For the remainder of this example, assume that the clinical data elements either as submitted ("clinical event details") or in the EHR ("EHR data elements") support testing but the medically appropriateness knowledge base suggests that conventional diagnostic testing is the appropriate care. The system would determine at block 912 if the clinical data elements in the integrated transaction indicate that conventional testing was performed. Since the new genetic test is not the conventional treatment, the system would provide notification to the provider at block 916 that the clinical event details do not satisfy the appropriateness criteria. In this case, assume the clinician opts for the new treatment. Since additional clinical data elements are irrelevant to the decision to use the new treatment, none are received at block 918. Next, the system would determine at block 922 if a reason for care is provided. In this case, the care provider provides input that a new procedure was employed. In an embodiment, the care provider interacts through a standard user interface including a number of reasons for departing from the appropriateness criteria defined identified at block 907. The user interface preferably includes a free text field for inputting additional reasons. In this case, the user may select the option that a new genetic test is available. At block 924, the system would determine if this reason is acceptable. This determination may be made based solely on the reason received. Alternatively, the decision may be made based on a combination of other factors. In this case, the reason would be deemed appropriate and the medical appropriateness adjudication satisfied at block 914.

In another example, when a new disease (as opposed to a treatment) is discovered, a standard accepted set of appropriateness criteria will not be defined. By way of recent example, when persons first presented with Severe Acute Respiratory Syndrome (SARS), the system would have determined that appropriateness criteria were not defined at block 904. Also, at block 906, the system would store this determination to the integrated transaction.

Systems of the present invention may be configured to automatically reimburse for care provided for certain diagnoses irrespective of the appropriateness of the care provided. In other embodiments, a care provider may automatically receive reimbursement up to a certain level of care of undefined appropriateness. In another embodiment, integrated transactions for which medical appropriateness criteria are unknown may be placed in a queue for a decision-making group to determine whether the care is appropriate. In one example, a real-time collaboration session is initiated to resolve the outlier cases for which appropriateness criteria are undefined.

With reference to FIG. 2, once medical appropriateness is adjudicated at block 208, the system results the initial level of reimbursement at block 210. In an embodiment, the level of reimbursement is set by the plan information stored in the eligibility data store 172. In embodiments, the clinical event details are defined at a granular level associated with clinical records rather than traditional codes. This allows the reimbursement to be set based on the actual care provided rather than a summary represented by one or more codes or groups of codes ("groupers"). Also, since numerous alternative treatments may satisfy the medical appropriateness criteria, different levels of reimbursement may be dictated for the same presenting problem. Rather than resulting one level of reimbursement based on the diagnosis code (or other course definition of the clinical event), the level of reimbursement may be dictated by the actual healthcare services provided. While the refined medical appropriateness adjudication protects payers for unnecessary costs and healthcare consumers by defining a number of treatments paths supported by medical evidence and patient-specific data, the clinical event details may be used to fairly reimburse providers for care provided.

As long as the care is medically appropriate, the provider will receive reimbursement for the clinical steps required to provide care without financial penalty to the provider. Consumers are safer since evidence is utilized to determine medically appropriate care and variance is reduced. Payers are protected since inappropriate care is not reimbursed and the provision of appropriate care will eliminate downstream costs due to bad outcomes. Also, the system may be used to provide the latest medically information to care providers by updating the medical appropriateness criteria.

Next, at block 212, the level of reimbursement is adjusted based on the quality of care provided. A first exemplary method 1000 for adjudicating the integrated transaction based on the quality of care provided during the clinical event is illustrated in the flow diagram of FIG. 10. The method 1000 of FIG. 10 adjusts the level of reimbursement based on the quality of care provided. A second exemplary method 1100 for adjudicating the integrated transaction based on the historical quality of care associated with the integrated transaction is illustrated in the flow diagram of FIG. 11. In embodiments of the invention, one or both of the methods may be utilized to determine the adjustment in the reimbursement level based on the quality of care provided. In these and other embodiments, processing and adjudication based on quality, is performed by a quality engine 178 and associated quality knowledge base 180.

Figure 10:
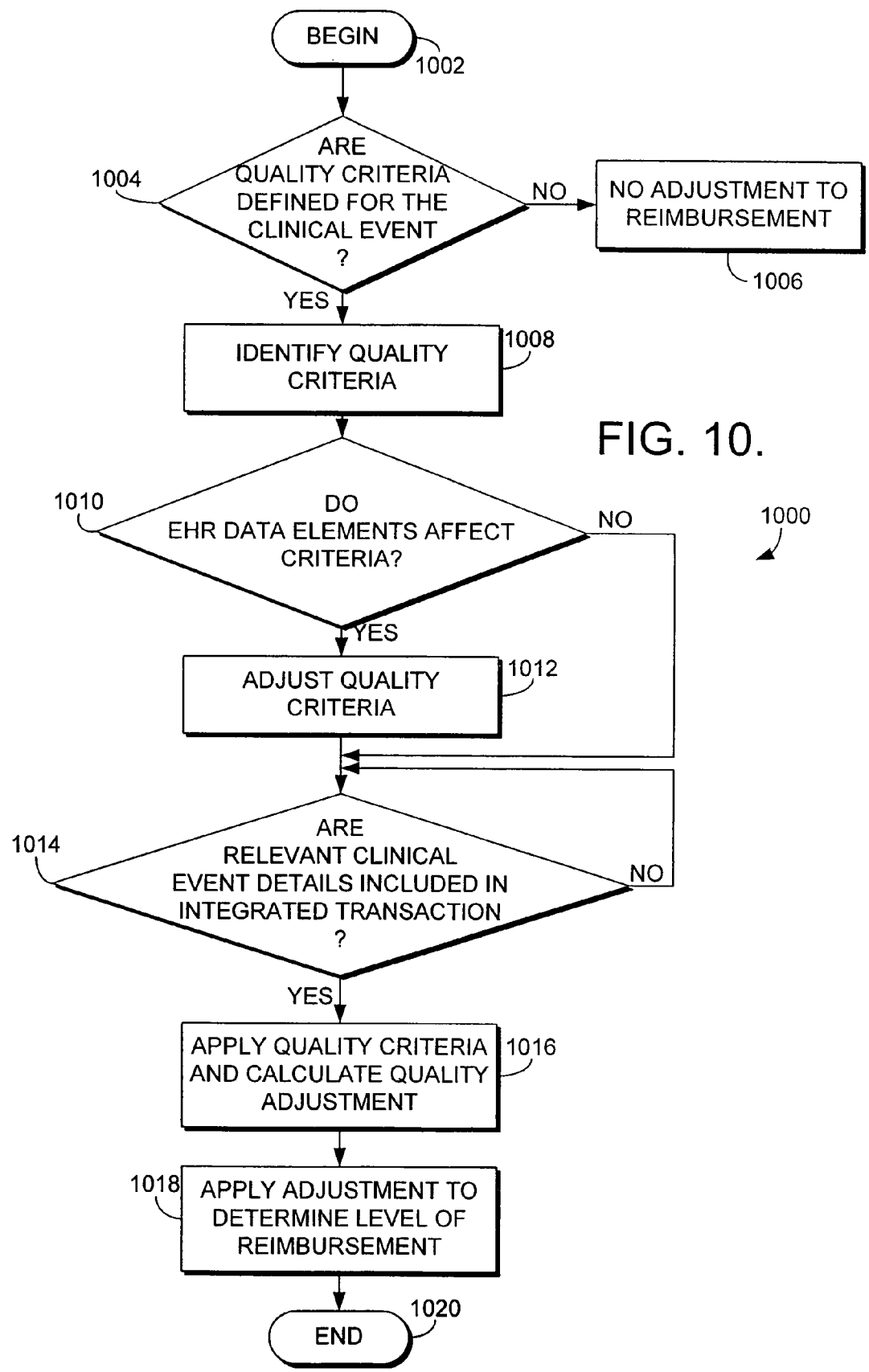
FIG. 10 is a flow chart representative of an exemplary computer program for adjudicating the integrated transaction based on the quality of care provided during the clinical event in accordance with an embodiment of the invention.

With reference to FIG. 10, method 1000 is initiated at block 1002. Next, at block 1004, the system determines if quality criteria are defined for the clinical event for which the integrated transaction originates. In embodiments, the quality criteria are organized and stored within quality knowledge base 180. Quality criteria include any of a number of measurable or observatable conditions indicating the relative success of the care. The criteria include the presence or absence of a clinical condition indicating an outcome. For example, without limitation, criteria include mortality, morbidity, length of visit or stay, onset of another condition due to poor care, recurrence, elimination of presenting problem, quality of life indicators, patient satisfaction, and unplanned Emergency Department (ED) visits due to poor care. Additional criteria such as those developed by the National Committee for Quality Assurance (NCQA) and the Joint Commission on Accreditation of Healthcare Organizations (JCAHO).

If the system determines that there are no quality criteria for the integrated transaction at block 1004, then no adjustment is made to the reimbursement at block 1006. If quality criteria are defined for the integrated transaction, the particular criteria are identified at block 1008. Next, at block 1010, the system determines if the EHR data elements in the integrated transaction affect the quality criteria. As set forth by example below, clinical conditions oftentimes affect the relevant measurement for quality. Rules to adjust the clinical criteria based on the presence or absence of EHR data elements are stored in quality knowledge base 180. In embodiments, these clinical conditions are stored in the EHR data store 160. Quality engine 178 analyzes the EHR data elements for the patient to determine if any of the rules are applicable. If EHR data elements in the integrated transaction affect the quality criteria, the rules are triggered and the criteria are adjusted accordingly at block 1012. If EHR data elements do not affect criteria as determined at block 1010, block 1012 is bypassed.

Next, at block 1014, the system determines if the relevant clinical data elements are part of the integrated transaction being adjudicated. If the relevant clinical event details are not present, the system continues to poll for the receipt of these data before a determination is made at block 1014. As set forth in FIG. 3 and discussed above, the present invention updates the integrated transaction at blocks 334 and 336 until all relevant clinical event details required for adjudication are available. As set forth below, the clinical event details evaluated by some quality criteria may be documented during the course of care or immediately thereafter. As such, the quality determination may be made in real time and the claim adjudicated on the basis of quality. If absent from the integrated transaction, a real time query may be made during the bypass loop for the care provider to document the clinical event details required for the quality adjudication.

Since quality data are oftentimes unavailable at the time care is provided, quality adjudication may be delayed until after the provision of care in some instances and embodiments. For instance, the time period between the presentation of a condition and the recurrence of the condition is not available during the initial provision of care. In these cases, the quality adjustment is not made until the recurrence occurs or after a pre-defined period elapses within which the condition does not recur. In embodiments, the quality portion of the reimbursement may be held until the clinical data elements required are aggregated in the integrated transaction. Alternatively, the provider may be reimbursed on the assumption that the care was of appropriate quality, and subsequently debited or credited to account for the quality of care provided when the appropriate data elements are added to the integrated transaction. Periodic queries of the persons or care providers may be made to complete the transaction.

Next, at block 1016, the system and method applies the quality criteria and calculates the quality adjustment. As set forth in the examples below, care of particularly poor quality may result in no reimbursement. More frequently, at block 1016, the quality component 120 applies an adjustment to the base level of reimbursement under the payer plan. Then, at block 1018, the calculation is made and the level of reimbursement is determined.

By way of a fictional example, a person presents to a care provider seeking treatment for a laceration to the arm causing excessive bleeding. The care provider treats the person by suturing the arm laceration with stitches. At this point, the bleeding has stopped, the laceration has been treated and the person is sent home. In embodiments, the system and method would determine if quality criteria were defined for this clinical event of the integrated transaction at block 1004. The criteria for this case could simply include the stoppage of bleeding, which would be identified at block 1008. After a determination is made whether there are relevant EHR data elements at block 1010, and whether relevant clinical data elements are included in the integrated transaction at block 1014, the quality determination is calculated at block 1016. In this case, the quality criteria are satisfied and a determination of the reimbursement level would be complete at block 1018.

Figure 11:
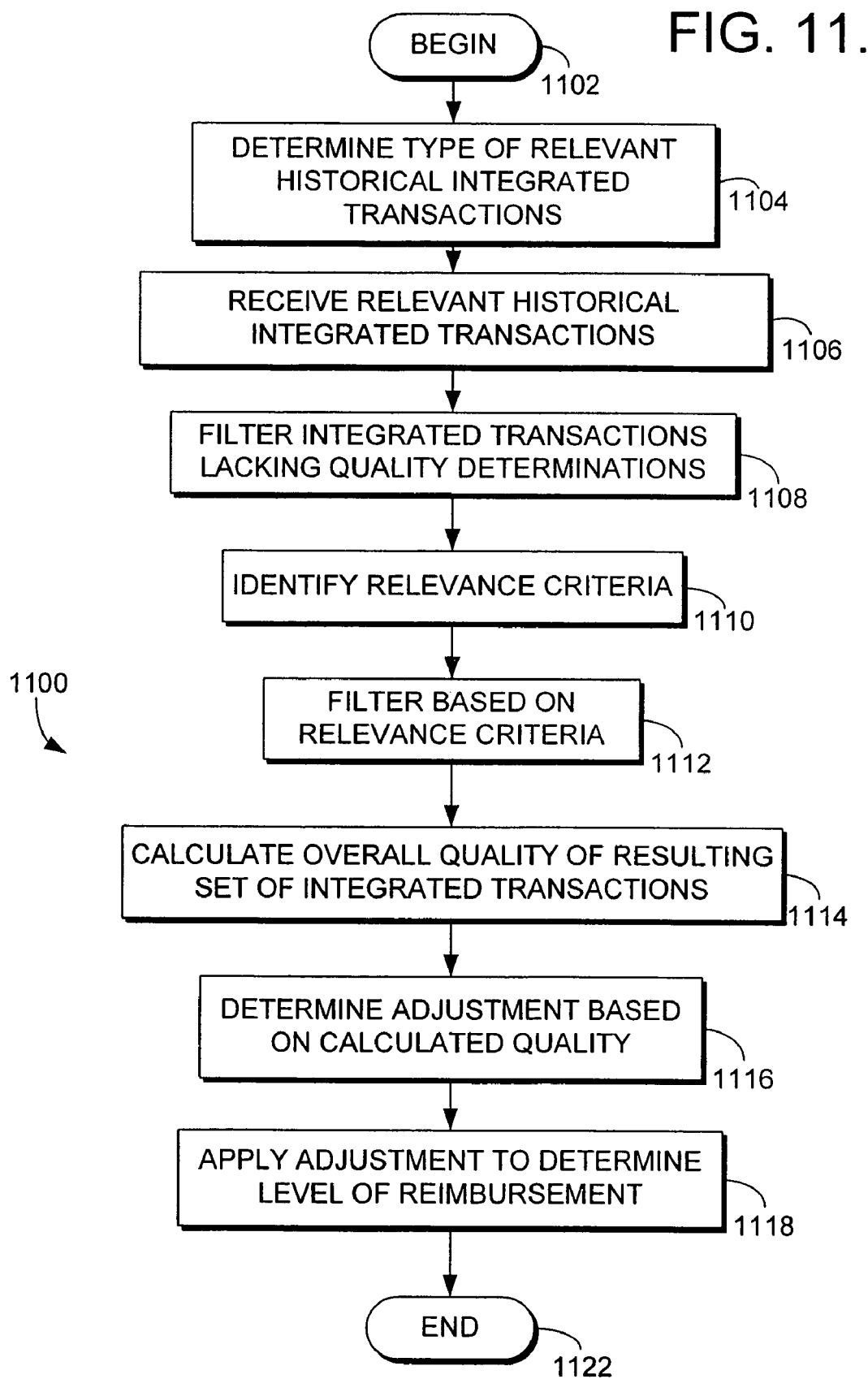
FIG. 11 is a flow chart representative of an exemplary computer program for adjudicating the integrated transaction based on the historical quality of care associated with the clinical event in accordance with an embodiment of the invention.

The exemplary method 1100 for adjudicating the integrated transaction based on the historical quality of care associated with the integrated transaction is illustrated in the flow diagram of FIG. 11. The method 1100 is initiated at block 1102 by quality module 120 (FIG. 1). Next, at block 1104, the system determines the type of historical integrated transactions are relevant to adjudicate the integrated transaction. In embodiments, the system will determine the type of relevant transactions based on the clinical data elements of the integrated transaction being adjudicated. For example, the type of relevant integrated transactions will oftentimes be limited to similar procedures for similar patients. Also, the type of relevant integrated transactions will be also be limited to those transactions submitted by a particular care provider, care provider's group or hospital at which the care was provided. For example, if the integrated transaction is related to a heart bypass surgery, the type of relevant transactions may be defined by heart bypass surgeries performed by an individual surgeon over the last two years. In another example, the type may be defined by all heart procedures performed by a particular group of doctors for a certain time period.

Next, at block 1106, the system receives (or identifies) integrated transactions of the appropriate type from the transaction data store 112. In an embodiment, integrated transaction data store 112 includes a data warehouse with predefined data marts of conventional data types to expedite the processing at block 1106.

Next, at block 1108, the system filters integrated transactions lacking quality determinations from the set of integrated transactions received at step 1106. Next, at block 1110, relevance criteria are identified. As set forth in the examples below, some of the filtered set of integrated transactions may lack relevance due to demographic information or other patient-specific clinical details stored in the integrated transactions. Also, some integrated transactions may not be relevant due to advances in medicine. If the quality criteria have changed based on the medical advances, then the care provided under the outdated method is not relevant. The relevance criteria may also limit the set of relevant integrated transactions to those occurring during a set period of time or to a set of the most recent transactions.

Next, at block 1112, the system filters the current set of relevant transactions based on the relevance criteria 1110 to define the relevant set of transactions upon which quality is used to adjudicate. Then, at block 1114, the system calculates the overall quality of the resulting set of integrated transactions. For example, the individual quality factors as determined by the process of FIG. 11 for each of the integrated transactions of the resulting set may be averaged to calculate an overall quality score.

Next, at block 1116, the system determines the adjustment based on the quality of care as calculated at block 1114. If the factors for a number of transactions are averaged at block 1116, then the averaged factor is used. If another calculation is employed at block 1114 to define the adjustment, an adjustment factor is determined at block 1116. Then, at block 1118, the calculation is made and the level of reimbursement is determined. In another embodiment, the reimbursement to the care provider could be issued as a bonus. Alternatively, a care provider could incur penalties for providing care of poor quality.

In one example, a forty year old male presents to a care provider with acute myocardial infarction. Initially, at block 1104, the system determines that the type of relevant historical integrated transactions related to diseases of the heart in adults 18-44 years of age connected to this particular care provider. At block 1106, the quality component receives the relevant transactions for further analysis. Next, at block 1108, the system filters those integrated transactions that lack quality determinations. At block 1110, the quality component then analyzes the integrated transactions to determine relevance to the originating integrated transaction. Data from the Centers for Disease Control and Prevention (CDC) indicates that the average hospital length of stay for adults 18-44 years of age for diseases of the heart is 3.7 days. Next, at block 1112, the system applies the CDC filters (age, heart disease) to define the relevant set of integrated transactions. At block 1114, the system calculates the length of stay for the set of integrated transactions and determines that this particular care provider averages 3.0 days for length of stay. This average is calculated from relevant integrated transactions from the previous twelve months. Next, at block 1116, the system determines the quality adjustment for the provider at a level of 1.23 by dividing the 3.7 days of the national average by the particular doctor's average of 3.0 days. Then, at block 1118, the system applies this 1.23 adjustment to determine the reimbursement level for the originating integrated transaction in this example. In additional embodiments, rather than using length of stay, the actual clinical event details used by clinicians to discharge patients could be evaluated to determine quality at a granular level.

As set forth above, methods 1000 and 1100 may be used simultaneously. For example, if adjustment factors are determined in both methods, both factors may be applied to the base level of reimbursement to account for the quality of the care provided in the integrated transaction being adjudicated and the quality of care historically provided by the care provider.

With reference to the previous example involving a forty year old male presenting with acute myocardial infarction, the system could make a quality adjustment based on historical transactions available in the central computing system. In addition, the system may make a quality adjustment simultaneously with the provision of care according to FIG. 10 for the specific length of stay for the patient. For example, as noted above, the quality adjustment based on relevant historical integrated transactions results in an adjustment factor of 1.23.If the person also had an actual length of stay of four days, the adjustment factor for the actual care may, in embodiments, be 0.93 (or 3.7 days of the national average divided by 4.0 days for the actual clinical event). When the historical adjustment factor of 1.23 and the actual factor of 0.93 are multiplied, an overall quality adjustment factor of 1.08 results for the integrated transaction. As such, if the appropriate level of reimbursement for this transaction is $1000, the provider would be reimbursed $1080.

With reference to FIG. 2, the system next determines if the adjudication criteria are satisfied at block 214. If the adjudication criteria are not satisfied, the integrated transaction is routed to a resolution queue at block 216. The adjudication criteria may not be satisfied if the originating integrated transaction is not eligible for reimbursement, the appropriateness criteria are not satisfied, or the quality factor is below a pre-defined threshold. In embodiments, reimbursement may be automatically refused rather than routed for further resolution if the adjudication criteria are not satisfied. If the adjudication criteria are satisfied, then the provider is automatically reimbursed at block 220 as described below with reference to FIG. 12.

Figure 12:
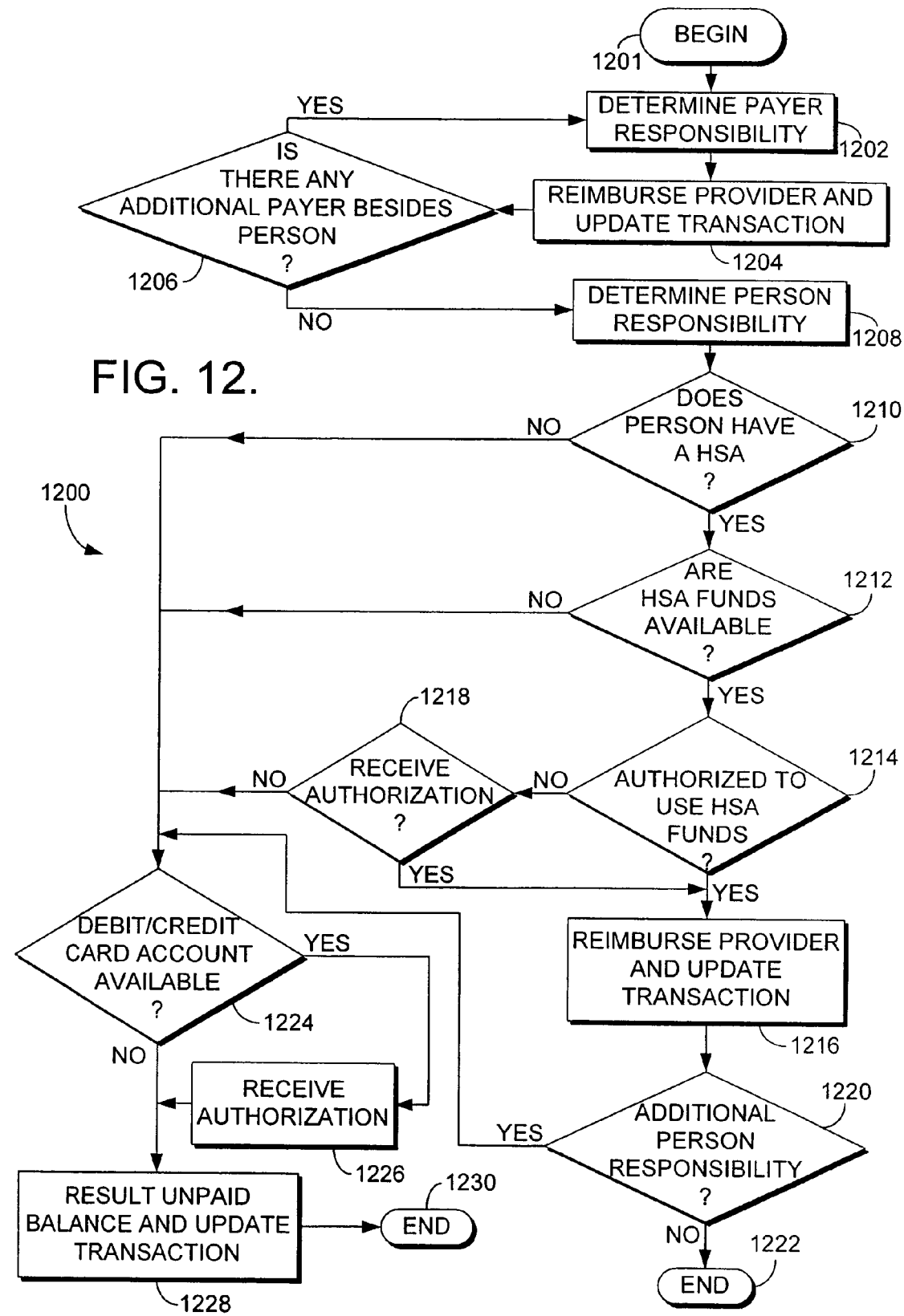
FIG. 12 is a flow chart representative of an exemplary computer program for automatically reimbursing the care provider based on the integrated transaction in accordance with an embodiment of the invention.

An exemplary method 1200 for automatically reimbursing the care provider based on the integrated transaction is illustrated in the flow diagram of FIG. 12. In embodiments, processing in accordance with the method is performed by reimbursement module 122 and related components. Namely, a reimbursement engine of reimbursement module 122 interacts with other components of central computing system 102 and a reimbursement data store 184 for storing data required to complete and record reimbursements.

Initially, at block 1201, the reimbursement process is initiated. Next, at block 1202, the system determines the responsibility of a primary payer. The responsibility is determined based on the plan information of the primary payer. The plan information preferably includes an appropriate baseline reimbursement amount for the care provided. In embodiments, as discussed herein, the reimbursement for each component of care provided is granular and relates to the actual care provided as detailed by the clinical details of each originating integrated transaction. The appropriate reimbursement amounts for each component of care documented in the integrated transaction are aggregated to determine the baseline level of reimbursement, and the baseline is adjusted on quality processing (and medical appropriateness, in embodiments) as set forth herein with reference to FIGS. 1-11. As such, in embodiments, due to the granularity of the transaction, the responsibility of each payer may be determined by parsing each transaction. For example, a first payer may have responsibility for procedures performed while a second payer has responsibility for medications costs. The system of the present invention could examine the clinical data elements to determine the level of responsibility of each payer based on the care provided and plan details. The parsing of the transaction and the plan details may determine the payer responsibility.

In embodiments of the invention, an initial level of reimbursement is determined at block 212 of FIG. 2 and individual payer responsibility at 1202 of FIG. 12. In embodiments, the processing to determine the level of reimbursement may be distributed between block 212 and the reimbursement method as illustrated in FIG. 12, particularly for adjudicating complex transactions.

Next, at block 1204, the provider is automatically reimbursed from an account from a primary payer. In embodiments, rather than automatically reimbursing the provider, the system initiates the reimbursement process. In embodiments, the payer is reimbursed in real-time via an electronic funds transfer (EFT). The payment details of the EFT are aggregated in the originating integrated transaction. EFT details and EFT processing are known to those of ordinary skill in the art.

Next, at block 1206, the system determines if there are any additional payers who may have responsibility for the remaining amount due for the originating integrated transaction. Multiple payers such as the government, a secondary insurer, or a charity may have responsibility for an individual clinical event. If there is a payer in addition to the primary payer, the reimbursement responsibility of the additional payer is determined at block 1202. As set forth with respect to the primary payer, the provider is automatically reimbursed from the additional payer at block 1204 and the integrated transaction is updated. This process continues at blocks 1206, 1202 and 1204 until reimbursements are received from each responsible payer. In a preferred embodiment, these payments are cumulated and processed in real-time or in near real-time to the care provider.

Once it is determined at block 1206 that there are no additional payers responsible for the care provided as detailed in the integrated transaction, the system subsequently determines the responsibility, if any, of the person receiving care (or the person responsible for payment) at block 1208. The responsibility of the person (or responsible person) is determined based on the plan details (as included in the integrated transaction or another component of the system). For instance, the person's responsibility may include a relatively small payment (co-pay) or a deductible against the responsibility of the payer(s) as determined at block 1202. Alternatively, the plan information may require the responsible person to pay a percentage of the overall amount of care provided. Next, at block 1210, the system determines if the person has a health spending account (or HSA). A health spending account is a personal account used for health expenditures. Examples of health spending accounts include Flexible Spending Accounts, Health Savings Accounts and Health Reimbursement Arrangements. The determination is made by querying one of any number of data stores that may include HSA information. In one example, the plan data in the eligibility module 116 includes HSA information for the persons associated with the plan. Alternatively, the system may query external data stores at the consumer 108 or financial institutions of the consumer to determine if the person has an HSA, particularly for Health Savings Accounts or other consumer-directed vehicles.

If the system determines that the person has an HSA, the system then determines whether funds are available in the HSA at block 1212. If funds are available, the system determines whether authorization has been given to withdraw HSA funds to pay for the person's responsibility at block 1214. In an embodiment, the reimbursement module 122 allows the consumer to establish a standing authorization to withdraw funds from the HSA based on any of a number of criteria. For example, the consumer may pre-authorize use of HSA funds for all of the person's responsibility. Since the integrated transaction includes a comprehensive set of clinical data elements and additional data elements, the user may pre-authorize payment from the HSA on a more detailed basis. In one example, the person may pre-authorize reimbursement for clinical events at a certain provider, of a certain type, or under a certain threshold payment amount, or any combination thereof. Additionally, the person may set pre-authorization conditions based on the quality (and/or appropriateness) factoring as determined in the processes of FIGS. 9-11. For example, authorization may be limited to care meeting for which quality is particularly high. These authorization criteria may be defined by interaction with the reimbursement module 122 through network 144 such as through a website or portal.

If the system is authorized to use HSA funds at block 1214, then the funds are used to reimburse the provider and the integrated transaction is updated at block 1216. If authorization has not been provided previously, at block 1218, the system determines if authorization is received directed for this particular integrated transaction. In an embodiment, the person may provide authorization at the care provider's site. This authorization may be provided by providing a password or personal identification number (PIN) similar to a conventional debit transaction. If authorization is received at block 1218, then the funds are used to reimburse the provider and the integrated transaction is updated at block 1216.

Next, at block 1220, the system determines if the person has additional financial responsibility. If not, then the reimbursement is complete and the process of FIG. 12 ends at block 1222.

If the system determines at block 1210 that the person does not have an HSA, or funds are not available at block 1212, or authorization to use funds is not received at block 1218, or that the person has additional responsibility at block 1220, then the system determines if a debit account or credit card account is available at block 1224. In an embodiment, the person provides this information to the reimbursement module 122. Alternatively, the information may be stored as part of the reimbursement data store 184.

If account information is available, the system determines if authorization is received for the integrated transaction at block 1226 in one of a number of ways known in the art. If authorization is received, the provider is automatically reimbursed and the integrated transaction is updated to include details related to the reimbursement such as amount, time, date and the like. If bank debit or credit card information is not available or if authorization is not received to use a bank debit or credit card, the integrated transaction is updated at block 1228 and the reimbursement process ends at block 1230. If automated reimbursement has not satisfied the amount due to the care provider, follow-up and reimbursement for the unpaid balance is the responsibility of the provider or provider institution.

Returning to FIG. 2, once the care provider is reimbursed at block 220 as described above, the process ends at block 222.

The system and methods of the present invention provide a number of advantages. For example, the ability to aggregate payer-based health care-related financial data, provider created clinical data, and medical evidence into a common platform has the potential to transform the manner by which care is delivered. The centralized operation reduces the redundant investment in information technology at the payers, providers and consumers, and allows each of the foregoing to monitor the information sourced from one another. The manual processing and reprocessing described in the background are obviated. The process of reimbursement is simplified. Providers have common access to the best clinical evidence, and the payers provide incentive to the providers to follow the best evidence. The aggregation of all of the integrated transactions in the central system creates a robust electronic medical record for the consumer, and a comprehensive data source from which research and community-based services may be provided. The invention thus reduces administrative costs and increases the quality of care by marrying patient-specific data, plan data from multiple payers and best medicine.

The foregoing description of the invention is illustrative, and modifications in configuration and implementation will occur to persons skilled in the art. Other hardware, software or other resources described as singular may, in embodiments, be distributed, and similarly in embodiments resources described as distributed may be combined. For example, the data stores in the central computing system may be stored in a single referential data base. The scope of the invention is accordingly intended to be limited only by the following claims.

What is claimed is:

1. One or more computer readable storage media having computer-executable instructions stored thereon that executes a method in a computing environment for adjudicating and reimbursing a care provider for services provided for a clinical event, comprising:

referencing an integrated transaction including a number of clinical data elements, wherein the clinical data elements comprise clinical event details electronically documented by the care provider at a point of care for the clinical event for which reimbursement is sought and electronic medical record data elements associated with a patient from an electronic medical record data store of a central computing system having historical electronic medical record data elements received from a plurality of sources;

accessing a data store including payer information;

determining whether at least a portion of medical care described in the integrated transaction is eligible for reimbursement by at least one payer by comparing the clinical data elements to plan information;

accessing a first knowledge base comprising evidence-based criteria for providing medically appropriate care, wherein the evidence-based criteria comprises one or more guidelines and standards;

selectively performing analysis of the clinical data elements of the integrated transaction against at least one evidence based criterion from the first knowledge base to determine if the care provided is medically appropriate;

accessing a second knowledge base comprising at least one quality criterion for assessing quality of health care, wherein the at least one quality criterion comprises a mortality, a morbidity, a length of visit or stay in a healthcare facility, an onset of another condition due to poor care, a recurrence, an elimination of a presenting problem, a quality of life indicator, a patient satisfaction, and an unplanned visit due to poor care;

selectively performing analysis of the clinical data elements of the integrated transaction against the at least one quality criterion to determine the quality of health care; and determining a level of reimbursement for a patient based on the determined medical appropriateness and the determined quality of the health care provided to the patient and authorizing reimbursement of the care provider from the at least one payer.

2. The media according to claim 1, further comprising storing the integrated transaction in a data store containing a number of transactions.

3. The media according to claim 2, further comprising providing consumer access to the stored transactions.

4. The media according to claim 1, further comprising reimbursing the care provider in real-time.

5. The media according to claim 1, further comprising receiving a number of transactions from a number of care providers.

6. The media according to claim 1, further comprising receiving payer information from a number of payers.

7. A method of generating an integrated transaction, the method comprising:

in a computing environment, referencing a number of clinical data elements comprising clinical event details provided by a care provider describing healthcare services provided and electronic medical record data elements associated with a patient from an electronic medical record data store of a central computing system having historical electronic medical record data elements received from a plurality of sources;

determining eligibility for reimbursement based on the clinical data elements as compared to stored plan information;

selectively performing a comparative analysis of the clinical data elements against a first knowledge base to determine medical appropriateness, wherein the first knowledge base includes appropriateness criteria comprising one or more guidelines and standards;

selectively performing a comparative analysis of the clinical data elements against a second knowledge base to determine quality of care, wherein the second knowledge base comprises quality of care criteria comprising one or more of a mortality, a morbidity, a length of visit or stay in a healthcare facility, an onset of another condition due to poor care, a recurrence, an elimination of presenting problem, a quality of life indicator, a patient satisfaction, and an unplanned visit due to poor care; and determining a level of reimbursement for a patient based on the determined eligibility, the determined medical appropriateness, and the determined quality of health care provided to the patient.

8. The method according to claim 7, wherein the step of receiving clinical data elements further comprises receiving administrative and financial data elements.

9. A computerized system for adjudicating and reimbursing a care provider for healthcare services in a computing environment, comprising:

a processing unit; and a memory for storing computer-executable instructions that when executed by the processing unit executes:

a first interface adapted to receive a number of transactions from a number of care providers, wherein each transaction includes clinical data elements comprising clinical event details captured during provision of the healthcare services, wherein the clinical data elements further comprise electronic medical record data elements associated with the patient from an electronic medical record data store of a central computing system having historical electronic medical record data elements received from a plurality of sources;

an eligibility engine configured to analyze the transaction to determine if the transaction is eligible for reimbursement by comparing the clinical data elements to stored plan information;

a first knowledge base comprising a set of clinical guidelines;

an appropriateness engine configured to selectively perform comparative analysis of the clinical data elements against the first knowledge base to determine medical appropriateness of the care provided;

a second knowledge base comprising a set of quality criteria, wherein the set of quality criteria comprises one or more of a mortality, a morbidity, a length of visit or stay in a healthcare facility, an onset of another condition due to poor care, a recurrence, an elimination of presenting problem, a quality of life indicator, a patient satisfaction, and an unplanned visit due to poor care;

a quality engine configured to selectively perform comparative analysis of the clinical data elements against the second knowledge base to determine the quality of the health care provided; and a reimbursement module for determining a level of reimbursement for the transaction for a patient based on the determined eligibility, the determined medical appropriateness, and the determined quality of the health care provided to the patient.

10. One or more computer readable storage media having computer-executable instructions stored thereon that executes a method in a computing environment for providing a community electronic medical record, comprising:

receiving a number of transactions from a number of providers requesting reimbursement for healthcare services, each transaction including clinical data elements comprising clinical event details captured during provision of the healthcare services, wherein the clinical data elements further comprise electronic medical record data elements associated with a patient from an electronic medical record data store of a central computing system having historical electronic medical record data elements received from a plurality of sources;

associating each transaction with a unique person identifier corresponding with a patient;

selectively performing a comparative analysis of the clinical data elements against a knowledge base to determine quality of care provided to a particular patient, wherein the second knowledge base comprises one or more quality of care criteria comprising a mortality, a morbidity, a length of visit or stay in a healthcare facility, an onset of another condition due to poor care, a recurrence, an elimination of a presenting problem, a quality of life indicator, a patient satisfaction, and an unplanned visit due to poor care;

determining a level of reimbursement for each transaction for the particular patient based at least on the determined quality of health care provided to the particular patient; and storing the transactions and selectively providing access to the transactions to the healthcare providers.

11. The media according to claim 10, wherein the transactions are in a standard pre-defined format.

12. The media according to claim 11, wherein a portion of the clinical data elements of the transactions are organized in structured charts.

13. The media according to claim 10, wherein the step of determining the level of reimbursement comprises determining eligibility of the transaction and analyzing the clinical data elements of the transaction to determine medical appropriateness of the healthcare services provided.

14. The media according to claim 13, wherein the step of determining the level of reimbursement further comprises analyzing the clinical data elements of the transaction to determine the quality of the healthcare services provided.

15. The media according to claim 10, further comprising the step of selectively providing access to the transactions to a number of payers.

16. The media according to claim 10, further comprising the step of selectively providing access to the transactions to a number of consumers.

* * * * *